(12) United States Patent
Bullard

(10) Patent No.: US 12,193,946 B2
(45) Date of Patent: *Jan. 14, 2025

(54) SYSTEMS AND METHODS FOR ADJACENT VERTEBRAL FIXATION

(71) Applicant: Absolute Advantage Medical LLC, Southern Pines, NC (US)

(72) Inventor: Dennis E. Bullard, Raleigh, NC (US)

(73) Assignee: Absolute Advantage Medical LLC, Southern Pines, NC (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/533,661

(22) Filed: Nov. 23, 2021

(65) Prior Publication Data
US 2022/0079773 A1 Mar. 17, 2022

Related U.S. Application Data

(63) Continuation of application No. 16/564,145, filed on Sep. 9, 2019, now Pat. No. 11,185,422, which is a
(Continued)

(51) Int. Cl.
*A61B 17/88* (2006.01)
*A61B 17/17* (2006.01)
(Continued)

(52) U.S. Cl.
CPC ........ *A61F 2/4455* (2013.01); *A61B 17/1728* (2013.01); *A61B 17/1757* (2013.01); *A61B 17/8042* (2013.01); *A61F 2/4611* (2013.01); *A61B 2017/564* (2013.01); *A61F 2/442* (2013.01); *A61F 2002/448* (2013.01);
(Continued)

(58) Field of Classification Search
CPC ...... A61F 2/4455; A61F 2/4611; A61F 2/442; A61F 2/46; A61F 2/4603; A61F 2002/448; A61F 2220/0025; A61B 17/1728; A61B 17/1757; A61B 17/8042; A61B 2017/564
USPC ...... 606/86 A, 86 B, 246, 247, 279, 280, 70, 606/71, 281, 286, 301, 302, 304, 305, 606/306, 307, 308, 319, 321, 322, 323, 606/92–95, 96, 99, 104
See application file for complete search history.

(56) References Cited

U.S. PATENT DOCUMENTS 9,987,145 B2 * 6/2018 Williams ................ A61F 2/447
10,433,978 B2 10/2019 Bullard
(Continued)

FOREIGN PATENT DOCUMENTS

JP 2009518090 A * 5/2009 ............ A61F 2/4611

OTHER PUBLICATIONS

JP 2009518090 (Year: 2009).*

*Primary Examiner* — Eduardo C Robert
*Assistant Examiner* — David C Comstock
(74) *Attorney, Agent, or Firm* — Troutman Pepper Hamilton Sanders LLP; James E. Schutz; Brandon M. Reed

(57) ABSTRACT

Systems and methods for spinal fusion procedures are described. The system in particular includes an intervertebral fixation system a positioning handle comprising a shaft. The distal end of the shaft includes a first locking mechanism that engages with a second locking mechanism of an implant. The system includes a holder including a handle channel. At least a portion of the shaft is insertable through the handle channel.

19 Claims, 20 Drawing Sheets

Related U.S. Application Data continuation of application No. 15/610,105, filed on May 31, 2017, now Pat. No. 10,433,978.

(60) Provisional application No. 62/343,483, filed on May 31, 2016.

(51) Int. Cl.
*A61B 17/70* (2006.01)
*A61B 17/80* (2006.01)
*A61F 2/44* (2006.01)
*A61F 2/46* (2006.01)
*A61B 17/56* (2006.01)

(52) U.S. Cl.
CPC .............. *A61F 2/46* (2013.01); *A61F 2/4603* (2013.01); *A61F 2220/0025* (2013.01)

(56) References Cited

U.S. PATENT DOCUMENTS

| | | |
|---|---|---|
| 2004/0186482 A1 | 9/2004 | Kolb et al. |
| 2006/0100637 A1 | 5/2006 | Rathbun et al. |
| 2009/0024132 A1 | 1/2009 | Blain et al. |
| 2010/0042167 A1* | 2/2010 | Nebosky ............... A61M 37/00 606/301 |
| 2011/0230970 A1 | 9/2011 | Lynn et al. |
| 2012/0116466 A1 | 5/2012 | Dinville et al. |
| 2012/0136392 A1 | 5/2012 | Keegan et al. |
| 2012/0143263 A1* | 6/2012 | Darendeliler ........ A61B 17/864 606/305 |
| 2015/0100126 A1* | 4/2015 | Melkent ............. A61B 17/8042 623/17.16 |
| 2015/0202051 A1 | 7/2015 | Tanaka et al. |
| 2016/0235448 A1 | 8/2016 | Seex |

\* cited by examiner

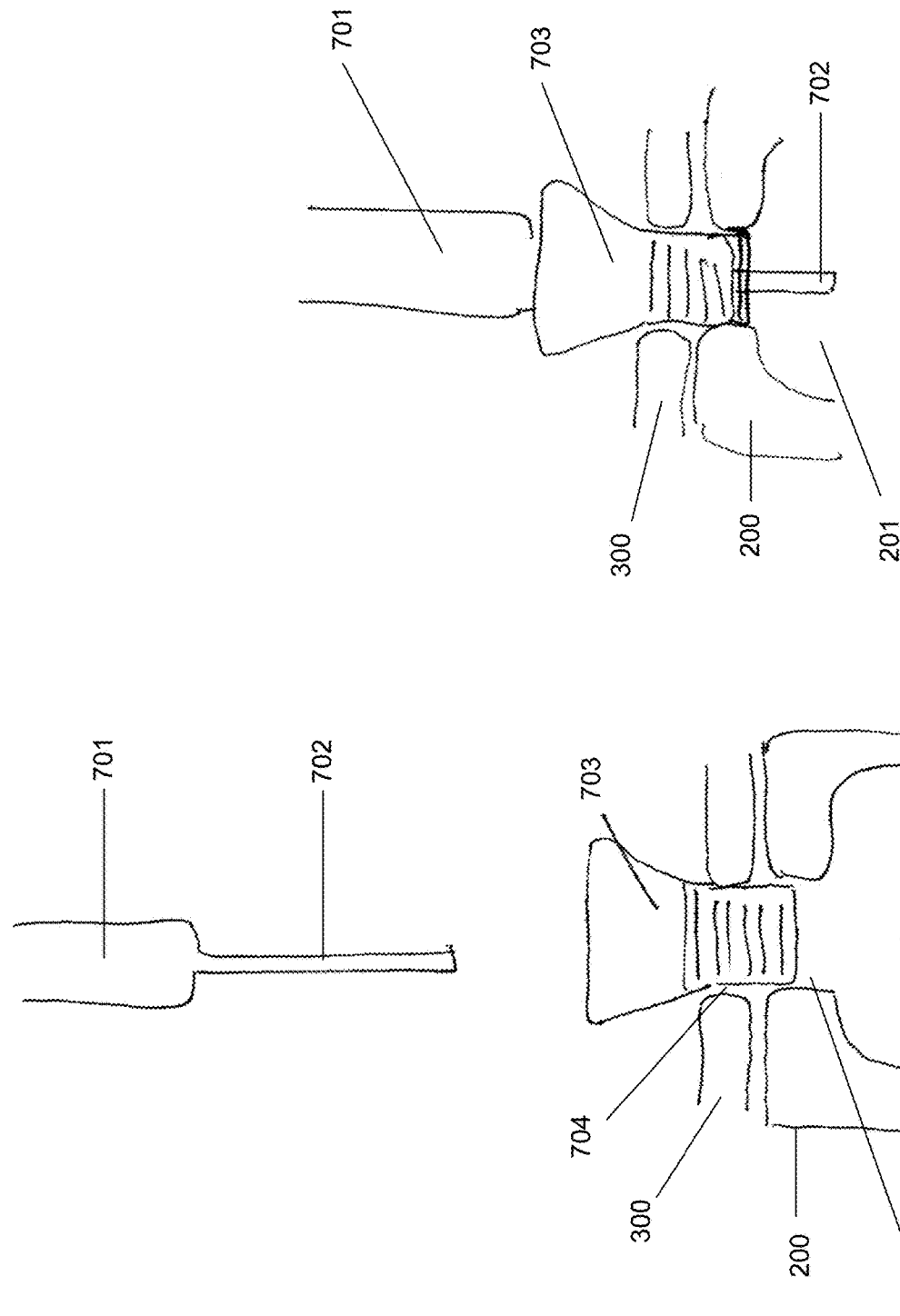

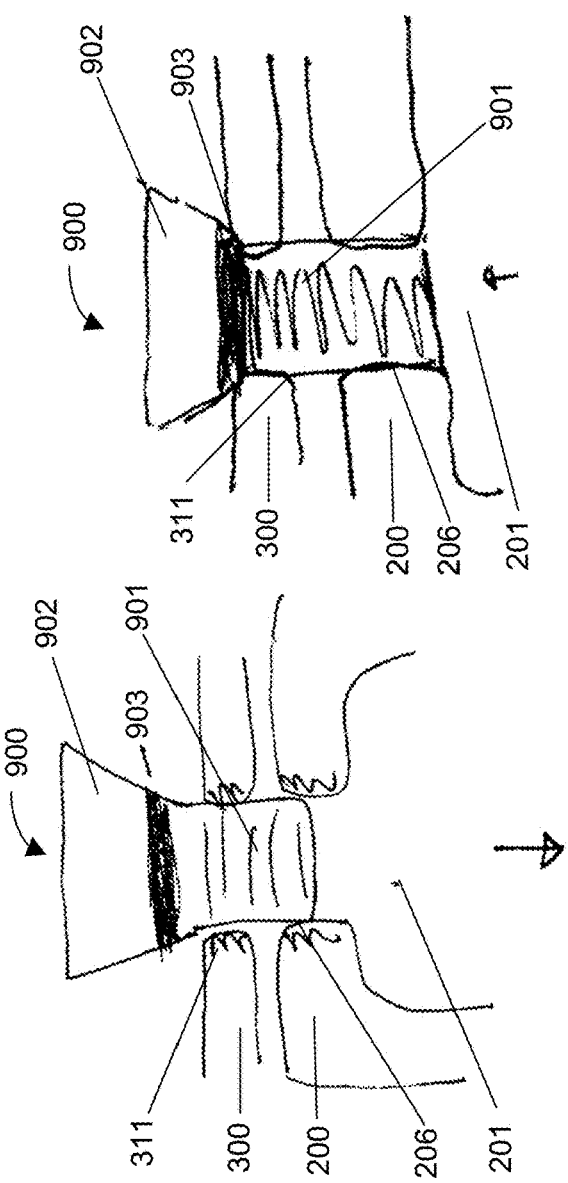

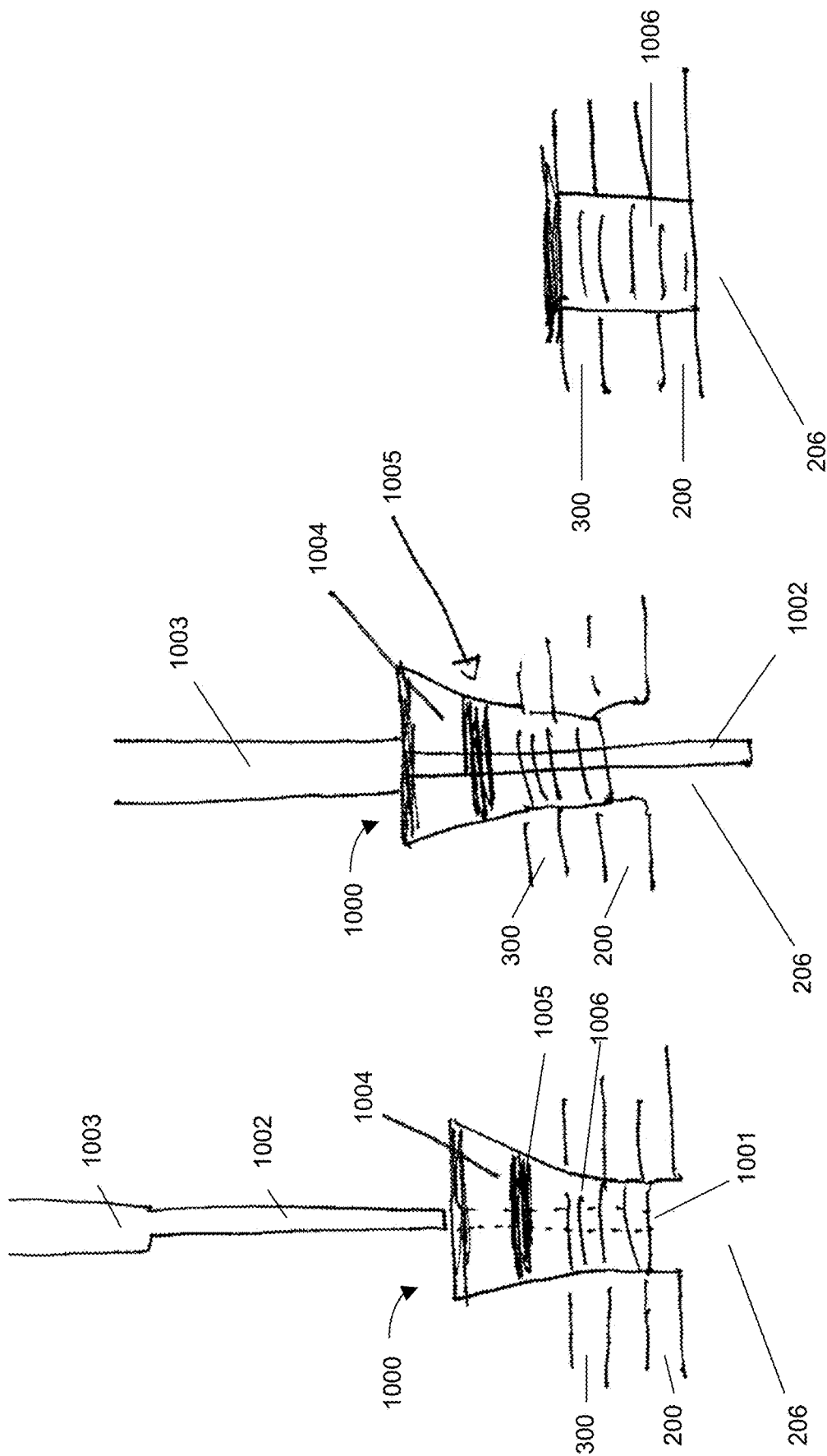

SYSTEMS AND METHODS FOR ADJACENT VERTEBRAL FIXATION

CROSS REFERENCE TO RELATED APPLICATIONS

This application is a continuation of, and claims priority under 35 U.S.C. § 120 to, U.S. patent application Ser. No. 16/564,145, filed 9 Sep. 2019, which is a continuation of U.S. patent application Ser. No. 15/610,105, filed 31 May 2017, now U.S. Pat. No. 10,433,978, which claims benefit to U.S. Provisional Application No. 62/343,483, filed 31 May 2016. The entire contents and substance of the above applications are hereby incorporated by reference as if fully set forth herein.

TECHNICAL FIELD

The present disclosed technology is primarily applicable to adjacent vertebral fixation; however it is also applicable to the fields of orthopedic surgery and biotechnology, as would be recognized by a person of ordinary skill in the art.

BACKGROUND

In the field of adjacent vertebral fixation, temporary pins have many disadvantages. If they are small, they do not hold the plate securely. If they are large, the same is often true but they also create cavities in the vertebral bodies. Additionally, it is preferable for the plate to be flush with the vertebral bodies to prevent the plate from acting as a lever and pulling out the pins when the plate is manipulated.

What is needed, therefore, is a vertebral fixation system that allows for adjacent vertebral fixation without the need to use temporary pins. Embodiments of the present invention address this need as well as other needs that will become apparent upon reading the description below in conjunction with the drawings.

BRIEF SUMMARY

Some embodiments of the present invention include a vertebral stabilization system comprising a positioning handle comprising a shaft with a distal end and a proximal end, the distal end of the shaft comprising a first locking mechanism, a cage-plate holder comprising a handle channel, the handle channel having an inner diameter approximately equal to the outer diameter of the positioning handle, such that a portion of the shaft can be inserted into the handle channel, a drill guide assembly comprising an opening from proximal to distal end of the drill guide assembly, and wherein the opening of the drill guide assembly is configured to accept a drill, a vertebral stabilization plate comprising a handle hole and an opening, wherein an inner diameter of the handle hole is approximately equal to the outer diameter of the distal end of the shaft of the positioning handle, such that distal end of the shaft of the positioning handle can be inserted into the handle hole, and wherein the opening of the plate is substantially aligned with the placement of the opening of the drill guide assembly, and an intervertebral cage comprising a distal end, a proximal end, and an opening, wherein the proximal end comprises an orifice with a second locking mechanism configured to lock with the first locking mechanism of the distal end of the shaft of the positioning handle, and wherein the opening of the cage extends from the superior side of the cage to the inferior side of the cage.

In some embodiments, the positioning handle further comprises a fluid channel extending from the proximal to distal end of the positioning handle. In some embodiments, the proximal end of the shaft of the positioning handle further comprises a syringe receptacle. In some embodiments, the proximal end of the shaft further comprises a feed ramp. In some embodiments, the first locking mechanism of the shaft of the positioning handle comprises external screw threads, and wherein the second locking mechanism of the orifice of the cage comprises internal screw threads. In some embodiments, the first locking mechanism of the shaft of the positioning handle comprises a keyway, wherein the second locking mechanism of the orifice of the cage comprises a keyhole, and wherein the keyway is configured to lock in the keyhole. In some embodiments, the cage-plate holder comprises a handle. In some embodiments, the cage-plate holder further comprises said drill guide assembly. In some embodiments, the cage-plate holder further comprises a third interlocking mechanism, and the drill guide assembly further comprises a fourth interlocking mechanism, the third and fourth interlocking mechanisms configured to interlock with one another The present invention further includes a method for stabilizing a vertebral column comprising inserting a positioning handle through a handle channel of a cage-plate holder, the positioning handle comprising a shaft with a distal end and a proximal end, the distal end of the shaft comprising a first locking mechanism, attaching a drill guide assembly to the cage-plate holder, the drill guide assembly comprising an opening from proximal to distal end of the drill guide assembly, and wherein the opening of the drill guide assembly is configured to accept a drill, inserting the positioning handle into a vertebral stabilization plate, the plate comprising a handle hole and an opening, wherein an inner diameter of the handle hole is approximately equal to the outer diameter of the distal end of the shaft of the positioning handle, such that distal end of the shaft of the positioning handle can be inserted into the handle hole, and wherein the opening of the positioning handle is substantially aligned with the placement of the opening of the drill guide assembly, and interlocking the first locking mechanism of the distal end of the shaft with a second locking mechanism of an intervertebral cage, the cage comprising a distal end, a proximal end, and an opening, wherein the proximal end of the cage comprises an orifice with the second locking mechanism configured to lock with the first locking mechanism of the distal end of the shaft, and wherein the opening of the cage extends from the superior side of the cage to the inferior side of the cage, inserting the intervertebral cage into the intervertebral space of a patient, and inserting a screw through the opening of the drill guide assembly.

In some embodiments, the cage-plate holder comprises said drill guide assembly. In some embodiments, the drill guide assembly comprises a plurality of openings, wherein the intervertebral stabilization plate comprises a plurality of openings, wherein the openings of the plate are aligned with the location of the openings of the drill guide assembly, and wherein a screw is inserted into an opening of the drill guide assembly and into an opening of the plate. In some embodiments, the first locking mechanism of the shaft of the positioning handle comprises external screw threads, and wherein the second locking mechanism of the orifice of the cage comprises internal screw threads. In some embodiments, the first locking mechanism of the shaft comprises external screw threads, wherein the handle hole of the vertebral stabilization plate comprises internal screw threads, wherein the second locking mechanism of the intervertebral comprises internal screw threads, wherein the first locking mechanism of the shaft is threaded into the handle hole of the plate, and wherein the first locking mechanism of the shaft positioning handle is threaded into the second locking mechanism of the cage. In some embodiments, the first locking mechanism of the shaft of the positioning handle comprises a keyway, wherein the second locking mechanism of the orifice of the cage comprises a keyhole, and wherein the keyway is configured to lock in the keyhole.

Some embodiments further comprise disposing a material within the opening of the cage prior to disposing the cage into the patient. Some embodiments further comprise removing the first locking mechanism of the shaft from the orifice of the cage, inserting a syringe into the orifice of the cage, wherein the orifice of the cage extends into the opening of the cage, delivering fluid into the orifice of the cage and into the opening of the cage. In some embodiments, the positioning handle further comprises a fluid channel extending from the proximal end of the shaft to the distal end of the shaft, wherein the orifice of the cage extends into the opening of the cage, and wherein the proximal end of the shaft comprises a syringe receptacle configured to accept a syringe. Some embodiments further comprise inserting a syringe into the syringe receptacle of the shaft, and delivering fluid through the positioning handle, through the orifice of the cage, and into the opening of the cage. Some embodiments further comprise disposing a material within the opening of the cage prior to disposing the cage into the patient, inserting a syringe into the syringe receptacle of the shaft, and delivering fluid through the positioning handle, through the orifice of the cage, and into the opening of the cage. In some embodiments, the proximal end of the shaft further comprises a feed ramp.

The foregoing summarizes only a few aspects of the present invention and is not intended to be reflective of the full scope of the present invention. Additional features and advantages of the present invention are set forth in the following detailed description and drawings, may be apparent from the detailed description and drawings, or may be learned by practicing the present invention. Moreover, both the foregoing summary and following detailed description are exemplary and explanatory and are intended to provide further explanation of the presently disclosed invention as claimed.

BRIEF DESCRIPTION OF THE FIGURES

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

FIGS. 7A-7B depict an embodiment where a fluid substance can be introduced into the cavity in the intervertebral cage using a syringe inserted through an injection cap.

FIGS. 9A-9C depict a shearable cage fastener plug in accordance with an embodiment.

FIGS. 10A-10C depict a combination injection cap and shearable cage fastener plug in accordance with an embodiment.

FIG. 16C depicts inserting screws into the vertebrae adjacent to the intervertebral space the modular intervertebral fixation device is inserted into using the drill guide assembly of the cage plate holder.

FIG. 16D depicts the resulting installed intervertebral fixation plate and interbody cage.

DETAILED DESCRIPTION

Figure 1:
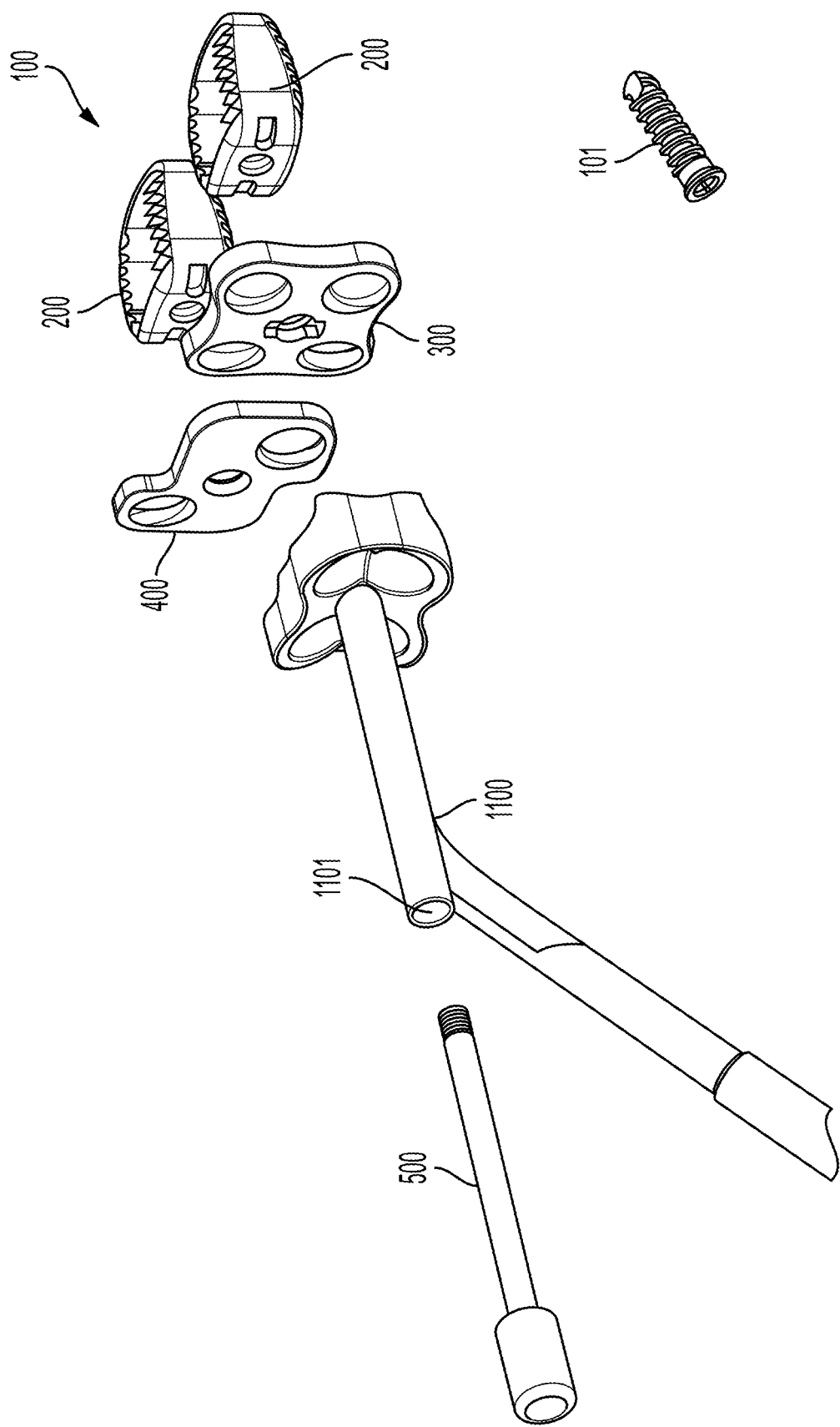
FIG. 1 is an exploded view of a modular vertebral fixation apparatus in accordance with an embodiment.

Although example embodiments of the disclosed technology are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It should also be noted that, as used in the specification and the appended claims, the singular forms "a," "an" and "the" include plural references unless the context clearly dictates otherwise. References to a composition containing "a" constituent is intended to include other constituents in addition to the one named.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the invention are intended to be illustrative and not restrictive. Many suitable components that would perform the same or similar functions as the components described herein are intended to be embraced within the scope of the invention. Such other components not described herein can include, but are not limited to, for example, similar components that are developed after development of the presently disclosed subject matter.

To facilitate an understanding of the principles and features of the invention, various illustrative embodiments are explained below. In particular, the presently disclosed subject matter is described in the context of a spinal fusion procedure. The present invention, however, is not so limited, and can be applicable in other contexts. Accordingly, when the present invention is described in the context of spinal fusion, it will be understood that other embodiments can take the place of those referred to.

The present disclosed technology includes a vertebral fixation system that can comprise a number of components that can be temporarily assembled to aid in the performance of a vertebral fixation procedure. In some embodiments, the vertebral fixation system can comprise a cage-plate holder, interbody cage ("cage"), vertebral fixation plate, drill guide assembly, and threaded handle. Prior to a procedure, a surgeon can assemble the vertebral fixation system into a single integrated unit by passing the threaded handle through the cage plate holder, and screwing on the vertebral fixation plate and cage.

Once assembled, and once a space has been made in an intervertebral space for insertion of the device, the cage can be inserted into an intervertebral space. Because the drill guide assembly and vertebral fixation plate are connected to the cage, the cage can maintain the alignment of vertebral fixation plate and drill guide assembly with the adjacent vertebrae. Because the cage provides this alignment function, temporary fixation pins need not be used to maintain alignment of the fixation plate and drill guide assembly.

In some embodiments, once holes are drilled in the adjacent vertebrae, bone screws can be inserted through the drill guide assembly and tightened into the drilled holes without the need to extract the drill guide assembly. Once the vertebral fixation plate is affixed to the adjacent vertebrae, the threaded handle can be un-screwed, and the cage plate holder removed. Once removed, the cage remains in an intervertebral space, and the vertebral fixation plate remains affixed to the adjacent vertebrae.

In some embodiments, an orifice in the cage, previously used to attach the cage to the cage plate holder, can be used to introduce a fluid substance, such as a bone growth promoter, into the intervertebral space. In some embodiments, an inactive, solid biologic material can be disposed in the central cavity of the cage, and inserted into a patient. After insertion, a fluid substance that activates the solid bone growth promoting material can be delivered through the orifice in the cage to active the inactive biologic material. In either case, the cage can serve to confine the fluid substance to the intervertebral space, and prevent contamination of adjacent anatomical features with the fluid substance. This fluid substance can be introduced in a variety of ways, as described below. In some embodiments, the fluid substance can be delivered through a threaded handle screwed into the orifice in the cage while the vertebral fixation system is still assembled. In some embodiments, the fluid substance can be delivered through the orifice after the removal of the cage plate holder.

FIG. 1 depicts the components of a vertebral fixation system in accordance with an embodiment. The fixation system can include a multi-screw vertebral fixation plate, such as a two-screw vertebral fixation plate 400 or a four-screw vertebral fixation plate 300, a cage 200, and one or more bone screws 101. The vertebral fixation system can be used to perform a spinal fusion procedure by inserting a cage 200 filled with a bone growth factor or active biologic agent into the intervertebral space of a patient, and affixing the vertebra above and below the cage using a vertebral fixation plate 300/400. To perform such a procedure, a surgeon can affix a cage 200 and a vertebral fixation plate 300/400 to a cage-plate holder 1100 using a threaded handle 500. The threaded handle can be inserted through a handle channel 1101 of the cage-plate holder 1100.

Figure 2B:
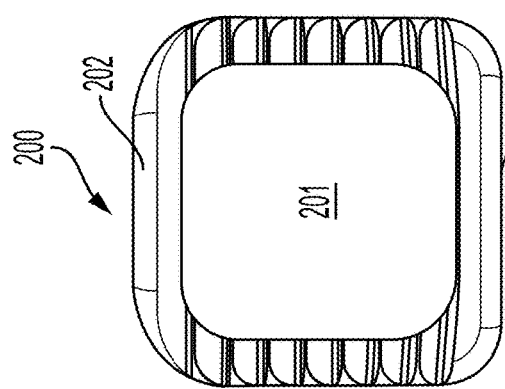
FIGS. 2A-D are various views of an intervertebral cage in accordance with an embodiment.
Figure 2D:
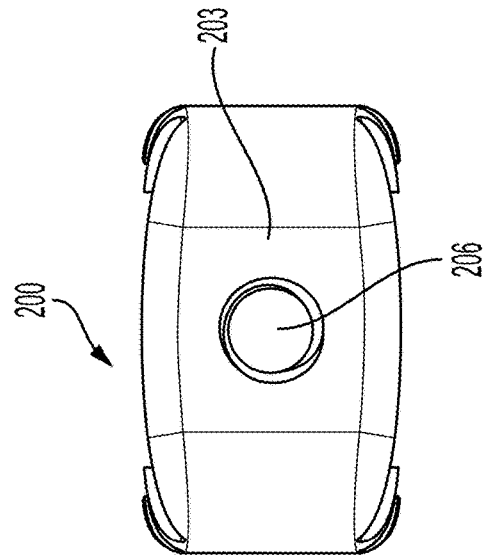
Figure 2A:
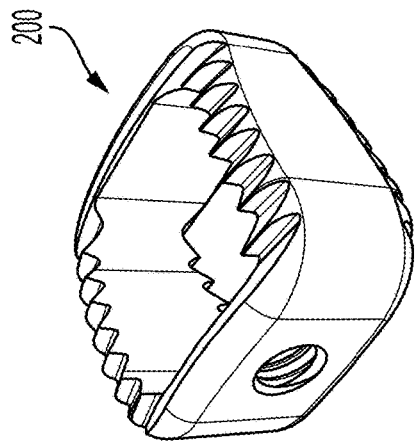
Figure 2C:
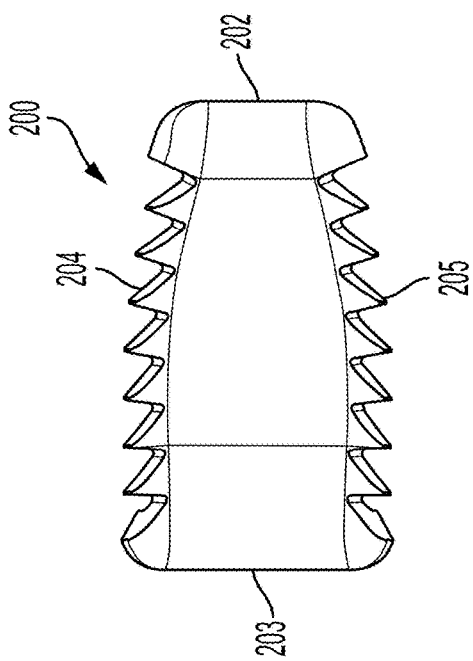

FIG. 2A-2D are views of an intervertebral cage 200 in accordance with an example embodiment. Cage 200 forms an enclosure, such as an approximately a square shape, with a cavity 201 in the center. In some embodiments, the outer edges of the cage 200 are rounded. In some embodiments, the inner surfaces of the cavity 201 are also rounded. In some embodiments, the distal end of the cage 200—furthest from the surgeon—can be narrower than the proximal end 203. In this case, the cage would form a trapezoid with the distal end 202 being the shortest edge. In some embodiments, Cage 200 can have a textured upper 204 and lower 205 surfaces to encourage bone growth and fixation of the cage when inserted in a patient. In some embodiments, cage 200 can have a tapered or wedge shape, such that the distal end 202 is slightly smaller than the proximate end 203, as shown in FIG. 2C. Cage 200 further has an orifice, or channel 206 in the proximal end of the cage. This orifice passes from the outer edge of proximal end 203 to cavity 201. In some embodiments, this orifice has threads on its inner surface, allowing the threaded end of threaded handle 500 to screw into Cage 200. Cage 200 can be made of materials such as titanium or Polyether ether ketone (PEEK), or can comprise bone allografts.

Figure 3A:
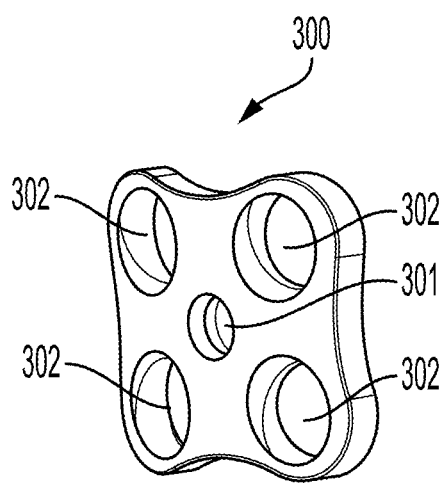
FIGS. 3A-B show a four-screw vertebral fixation plate with a center hole, in accordance with an embodiment.
Figure 3B:
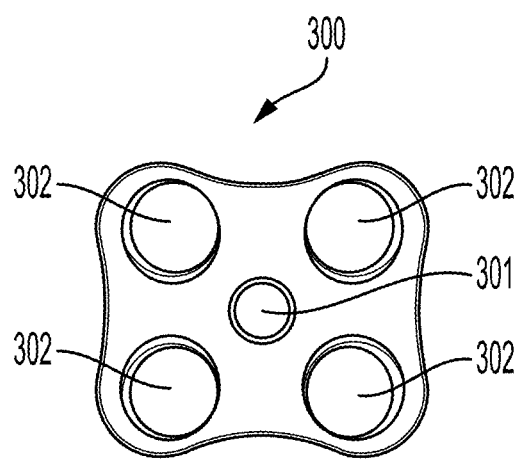

FIGS. 3A-3B depicts a four-screw vertebral fixation plate 300 in accordance with an embodiment. The vertebral fixation plate has a hole 301 through which a threaded handle 500 can be inserted. In some embodiments, the surface of hole 301 can be threaded. In some embodiments, the surface of hole 301 is not threaded. The vertebral fixation plate of an example embodiment has four screw holes 302. Each of these screw holes can be counter-sunk to match the head of a bone screw 101. In some embodiments, screw hole 302 is approximately the same size as the screw, fully constraining the position of the vertebral fixation plate 300 relative to the bone screw 101. In some embodiments, screw hole 302 can be elongate or semi-constrained, allowing the screw to move relative to the vertebral fixation plate when attached to a vertebra. The vertebral fixation plate can be used with an intervertebral cage 200.

Figure 4A:
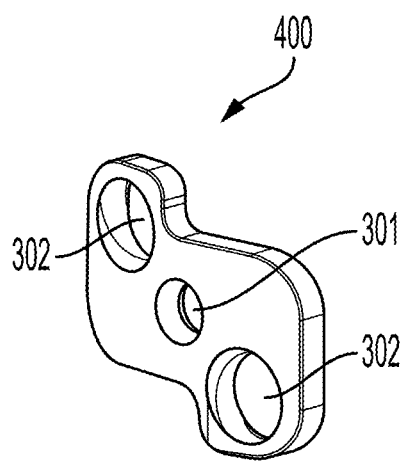
FIGS. 4A-B show a two-screw vertebral fixation plate with a center hole, in accordance with an embodiment.
Figure 4B:
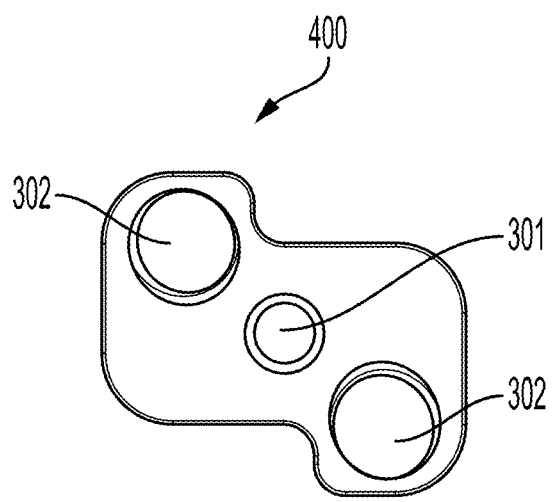

FIGS. 4A-4B depict a two-screw vertebral fixation plate 400 in accordance with an embodiment. The two-screw vertebral fixation plate 400 can have substantially the same features as the four-screw vertebral fixation plate 402, except it only has two screw holes 302. Alternatively, the fixation plate may have another suitable number of screw holes.

Figure 5A:
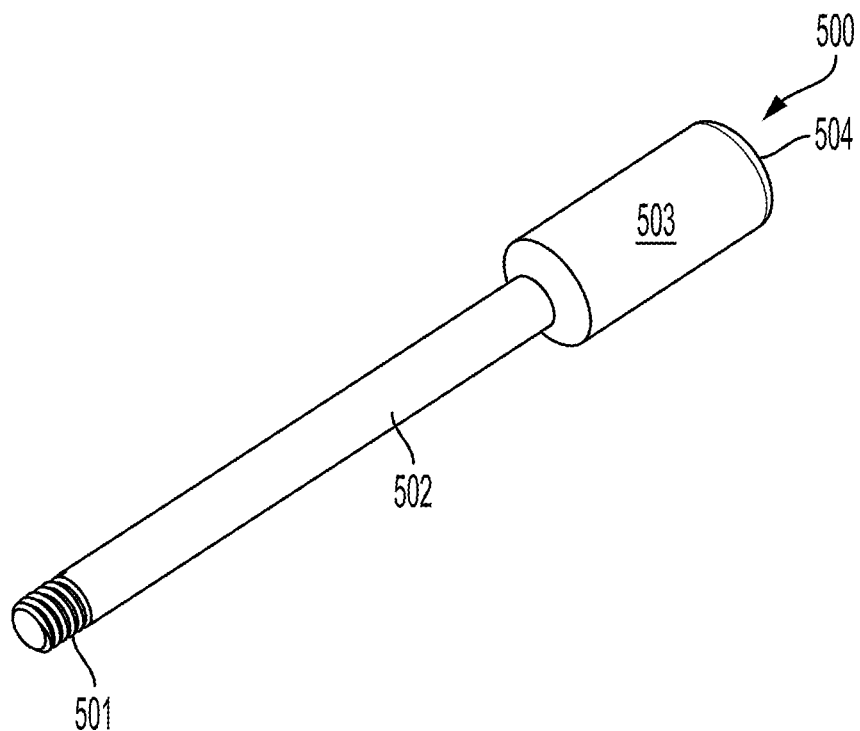
FIGS. 5A-B show a threaded handle in accordance with an embodiment, in accordance with an embodiment.
Figure 5B:
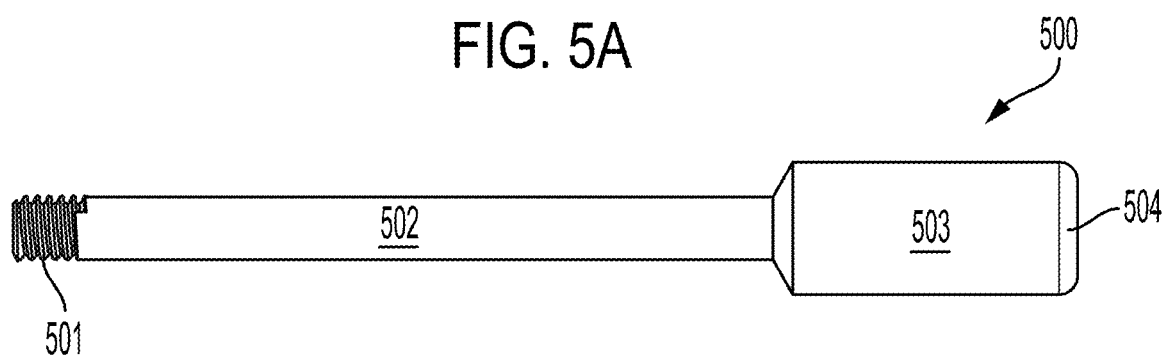

FIGS. 5A-5B depict threaded handle 500. In some embodiments, threaded handle 500 is used to connect the cage 200 to the cage plate holder 1100, vertebral fixation plate 300 or 400, and cage 200. Threaded handle 500 can have a threaded end 501 which can screw into orifice 206 of cage 200. The threaded end 501 can be substantially as long as the depth of the threaded orifice 206 in cage 200. In some embodiments, the threaded end 501 can be substantially as long as the sum of the thickness of the threaded orifice 206 in cage 200, and the thickness of hole 301 in the vertebral fixation plate 300 or 400, particularly when hole 301 is threaded. In some embodiments, the threaded handle 500 may have an alternative attachment mechanism for attachment to the cage 200 and/or vertebral fixation plate 300 or 400. For example, the threaded handle 500 may have a keyway that interlocks with a keyhole in the cage 200 or vertebral fixation plate 300 or 400. Other attachment mechanisms suitable for connecting threaded handle 500 to cage 200 or vertebral fixation plate 300 or 400 would be readily recognized by persons having ordinary skill in the art. Threaded handle 500 also has a shaft 502 which can extend through the cage plate holder 1100, and through the vertebral fixation plate 300 or 400. The diameter of shaft 502 can be approximately the interior diameter of the hole in the vertebral fixation plate 300 or 400, or the interior diameter of the central channel 1101 in cage plate holder 1100. When inserted into cage plate holder 1100, the threaded handle 500 should be able to slide within the central channel 1101 in cage plate holder 1100 with minimal play within the channel. In some embodiments, threaded handle 500 can have a handle 503, which allows the threaded handle to be manipulated by a surgeon. Handle 503 can also allow the entire assembled modular vertebral fixation system 100 to be manipulated by the surgeon. Threaded handle 500 can also have an impact surface 504 that allows the modular vertebral fixation system to be struck with a mallet to insert the cage into an intervertebral space.

Figure 6A:
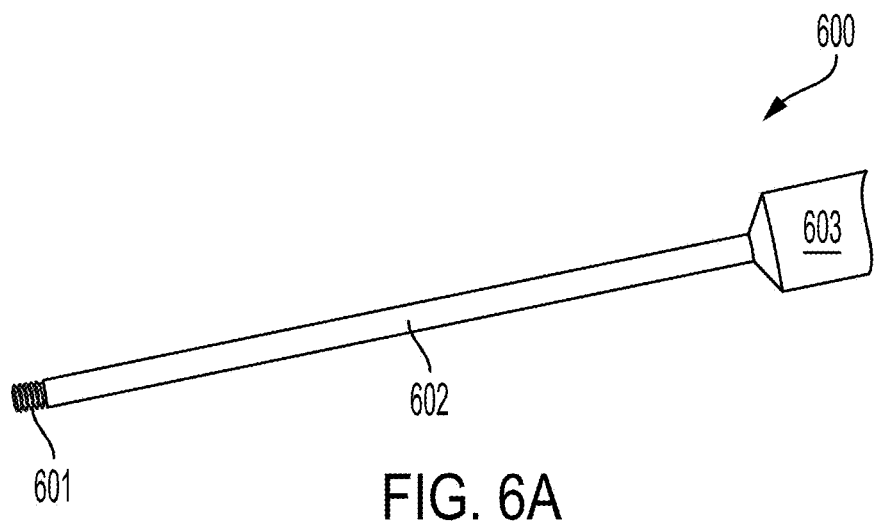
FIGS. 6A-6B show a threaded handle with a central channel in accordance with an embodiment.
Figure 6B:
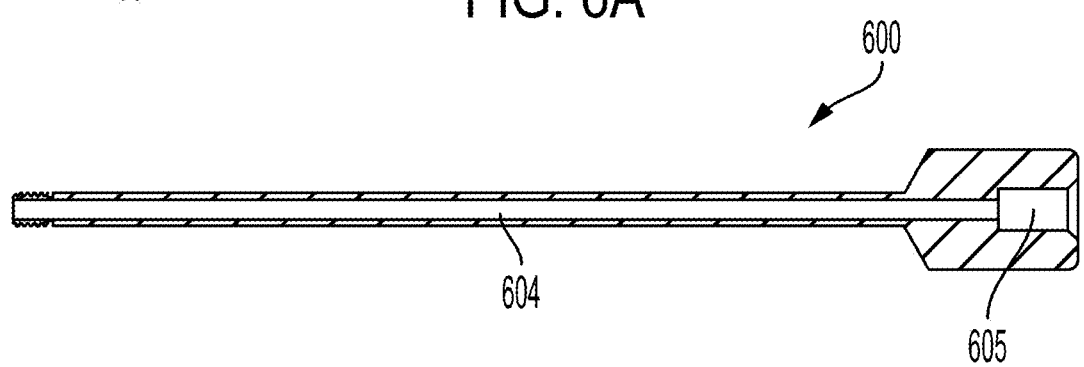
Figure 6C:
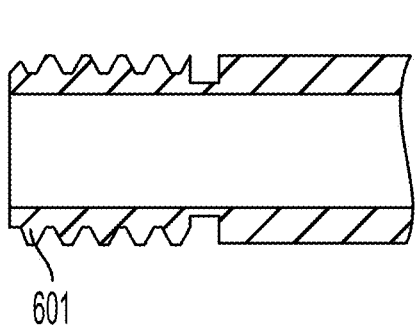
FIG. 6C is a detailed view of the threaded end of a threaded handle with a central channel, in accordance with an embodiment.
Figure 6D:
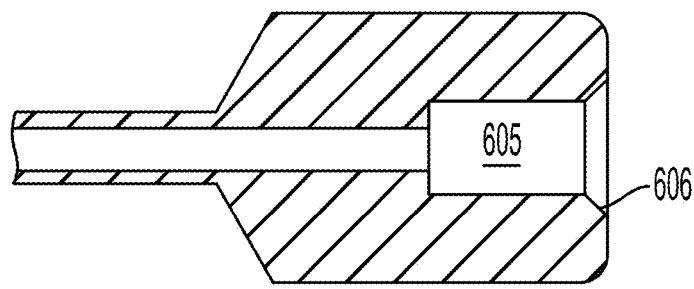
FIG. 6D is a detailed view of a syringe receptacle of a threaded handle with a central channel in accordance with an embodiment.

FIG. 6A-6B depict a threaded handle with a fluid channel 600 for use with an injectable substance. Like the first threaded handle 500, the threaded handle has a threaded end 601, a shaft 602, and a handle 603. In addition, the threaded handle with a fluid channel 600 can have a central fluid channel 604, and a syringe receptacle 605, as shown in FIG. 6B. The threaded end 601 is shown in more detail in FIG. 6C. The threaded end 601 is sized to screw into the orifice 206 of cage 200 and create a fluid-tight seal. To further facilitate the injection of a fluid substance into the cavity 201 of cage 200, the inside diameter of orifice 206 of cage 200 can be made smaller than the inside diameter of the center hole 301 of vertebral fixation plate 300. The shaft 602 of threaded handle 600 can then include a segment near the end where the outside diameter of the shaft changes from the smaller diameter matching the diameter of orifice 206 to a larger diameter that can fit through center hole 301 of vertebral fixation plate 300. In this way, when threaded handle 600 is inserted into the cage, it will not penetrate the cage any further than the length of the portion of shaft 602 which is smaller than the inside diameter of orifice 206.

The syringe receptacle 605 is disposed in the handle 603, and is designed to mate with a syringe containing a fluid substance. In some embodiments, the syringe receptacle 605 can be threaded, allowing a syringe to be screwed into the syringe receptacle 605. In some embodiments, the syringe receptacle can be smooth, and shaped to allow a syringe to be press-fit into the receptacle. A feed ramp 606 can facilitate the formation of a fluid-tight seal between the syringe receptacle 605 and the syringe. In some embodiments, the threaded handle with a fluid channel 600 can be made of stainless steel, or other suitable materials as would be recognized by one of skill in the art.

With these features, the threaded channel 600 can be used to inject a fluid substance into the cavity 201 of cage 200. For example, in some embodiments, the cage may be inserted into an intervertebral space of a patient with the cavity 201 empty, or with an inactive biological material. Once a surgeon has placed the cage 200, and affixed a vertebral fixation plate 300/400 with bone screws 101, a fluid substance can be introduced into the cavity 201. In some embodiments, the fluid substance can be a bone growth promoting biologic material, such as Infuse®. In some embodiments, the fluid substance can be an activation agent that activates the inactive biological material in cavity 201.

In some embodiments, the threaded handle with a fluid channel 600 can be used instead of a threaded handle without a fluid channel 500. In some embodiments, a protective cap can be placed over the syringe receptacle 605 to protect it from impaction. In some embodiments, a threaded handle without a fluid channel 500 may be replaced during the procedure by the threaded handle with a fluid channel 600 to allow a fluid to be injected into cavity 201.

FIGS. 7A-7B depict an embodiment where a fluid substance is introduced into cavity 201 via a separate syringe 701. The syringe 701 can be used after the cage plate holder 1100 and threaded handle 500 have been removed, but while the wound in the patient is still open. The syringe 701 can have a thin tip 702 for injecting through an injection cap 703. The injection cap can have a threaded or non-threaded distal end 704 which fits through orifice 206 in cage 200. The injection cap can be sized such that it is snug enough and extends into the cage sufficiently to insure a fluid tight seal. FIG. 7B depicts the insertion of thin tip 702 of syringe 701 through injection cap 703 such that the thin tip 702 is in fluid communication with the cavity 201 in cage 200.

Figure 8C:
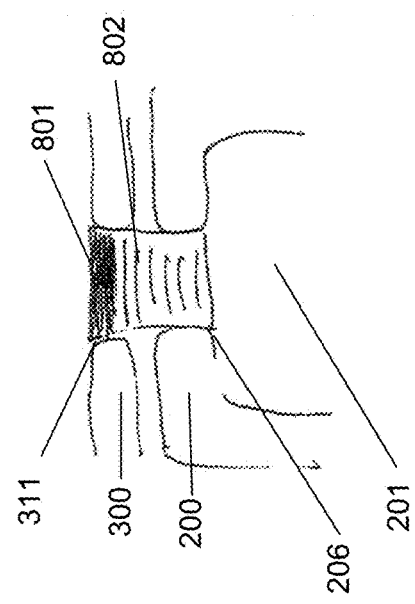
FIGS. 8A-8C depict a cage fastener plug in accordance with an embodiment.
Figure 8B:
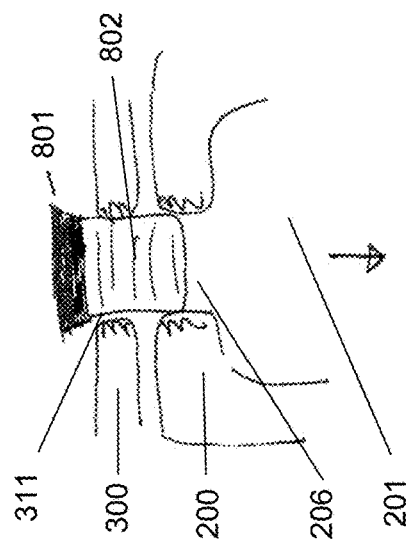
Figure 8A:
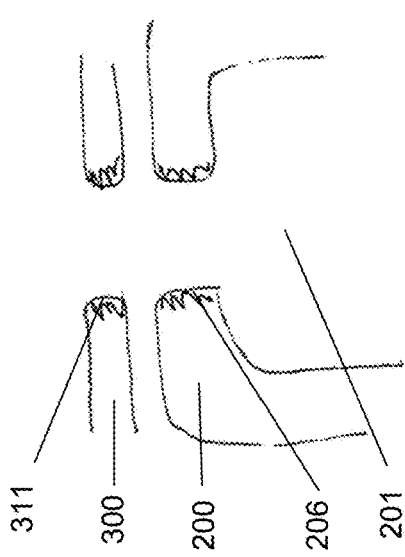

FIGS. 8A-C depict a cage fastener plug 801 in accordance with an embodiment. Once a fluid substance has been introduced into cavity 201 of cage 200, orifice 206 is still open, and can allow the fluid substance to leak out. FIG. 8A depicts the openings in the vertebral fixation plate 300 and cage 200 that lead to cavity 201. To seal these openings, an optional cage fastener plug 801 can be screwed into the orifice 206 of cage 200 to seal the cavity 201 of the cage 200, and retain the fluid substance, in some embodiments. This cage fastener plug 801 can have a threaded surface 802 which mates with a threaded inside surface of orifice 206 and also with threads on the inside of hole 301 in the vertebral fixation plate 300, as shown in FIG. 8B. When installed, the cage fastener plug creates a fluid tight seal with orifice 206, sealing cavity 201, and having a top surface that is flush with the upper surface of the vertebral fixation plate 300.

FIGS. 9A-9C depict an alternative shearable cage fastener plug 900 in accordance with an embodiment. Like the previous cage fastener plug, shearable cage fastener plug 900 can be screwed into the orifice 206 of cage 200 to seal the cavity 201 of the cage 200, and retain the fluid substance, in some embodiments. This shearable cage fastener plug 900 can have a threaded surface 901 which mates with a threaded inside surface of orifice 206 and also with threads on the inside of hole 301 in the vertebral fixation plate 300, as shown in FIG. 9A. When installed, the shearable cage fastener plug creates a fluid tight seal with orifice 206, sealing cavity 201, as shown in FIG. 9B. The shearable cage fastener plug 900 has a larger head 902 which can allow for easier manipulation of the screw, and easier installation in the cage within a patient. The shearable cage fastener plug also has a shearable zone 903 which breaks when a shearing force is applied to head 902, as shown in FIG. 9C.

FIGS. 10A-10C depict a combination injection cap and shearable cage fastener plug 1000. This combination fastener plug has a re-sealing opening 1001 which allows the thin tip 1002 of a syringe 1003 to pass through the combination fastener plug 1000 such that it is in fluid communication with orifice 206. Additionally, it has a larger head 1004 than the opening in vertebral fixation plate 300, and a shearing zone 1005. To use the combination fastener plug, the plug is first screwed into the vertebral fixation plate 300 and cage 200, as shown in FIG. 10A. Then, the thin tip 1002 of syringe 1003 is inserted through the injection cap 1000, allowing a fluid substance to be deposited in orifice 206, as shown in FIG. 10B. Finally, the head 1004 is sheared from the body of the combination fastener plug 1006, leaving a surface flush with the vertebral fixation plate 300.

Cage fasteners may be made of a similar material to that of the cage 200, such as titanium or PEEK. The fastener should be made of a material that does not create galvanic corrosion or produce free ions within the patent. In some embodiments, the orifice 206 of cage 200 is counter-sunk such that when installed, the outer surface of the fastener lies flush against the proximal surface 203 of cage 200. Further, the fastener plug should be designed such that it is prevented from touching the vertebral fixation plate 300 to prevent galling or particulate creation between the two if they abrade against each other.

Figure 11:
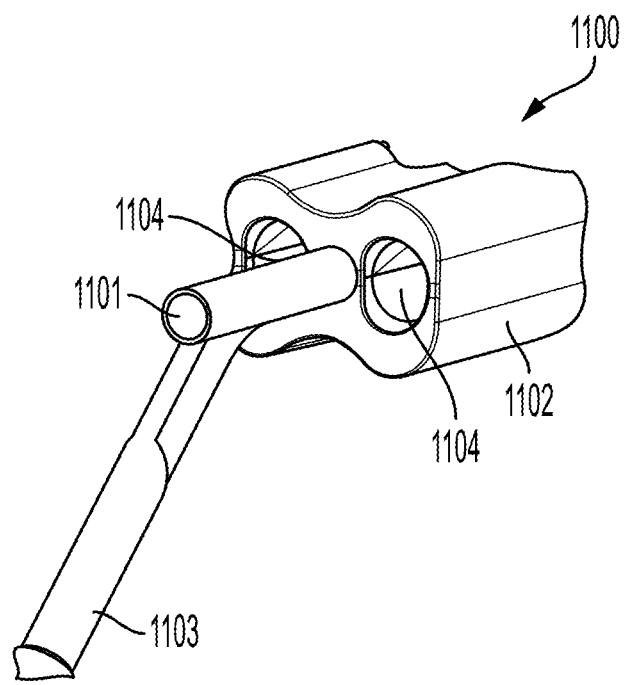
FIG. 11 depicts a cage plate holder in accordance with an embodiment.
Figure 12:
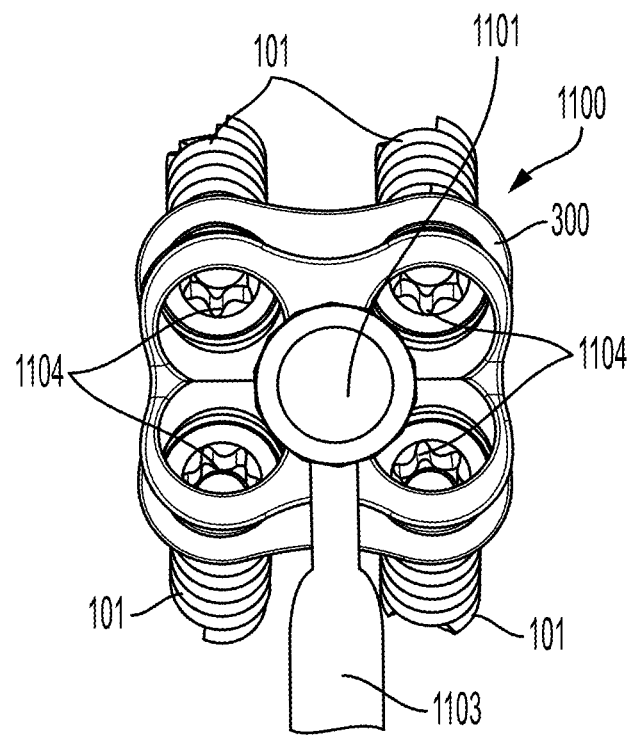
FIG. 12 depicts a cage plate holder in accordance with an embodiment with four screws are installed through the cage plate holder and into the intervertebral fixation plate.

FIGS. 11-12 depict a cage plate holder 1100 in accordance with an embodiment. Cage plate holder 1100 comprises a central channel 1101, drill guide assembly 1102, and handle 1103. The central channel is sized to accommodate the threaded handle 500 or 600. The handle 1103 can be any handle allowing a surgeon to manipulate the cage plate holder 1100 and is not entirely shown. Drill guide assembly 1102 allows a drill to be passed through, and holes to be drilled in vertebrae adjacent to the intervertebral space of a patient to be treated to allow the vertebral fixation plate 400 or 300 to be affixed to them via bone screws 101. In some embodiments, the drill guide assembly 1102 is welded or otherwise permanently attached to the central channel 1101. In some embodiments, the drill guide assembly 1102 can be snap-fit to the central channel 1101. Snap-fit drill guide assemblies can allow drill guides with varying screw angles or screw configurations to be quickly interchanged, and can minimize the footprint of the components in the surgical tray. The drill guide assembly has openings 1104 that allow a drill bit to be placed through the openings and exit the other side. In some embodiments, openings 1104 can be sized to allow for the use of awls, drills, and screws. In some embodiments, the openings 1104 will allow a surgeon to drill holes at varying angles with respect to the patient's dorsal direction, such as between 0-30 degrees, for example. In some embodiments, the openings 1104 will guide drills and screws in a predetermined, fixed angle. The openings are also sized such that bone screws 101 can be inserted through openings 1104 and installed in a vertebral fixation plate 101/300. FIG. 12 depicts a cage plate holder 1100 where used with a four-screw vertebral fixation plate 300. This figured depicts that screws may be inserted through openings 1104 and through vertebral fixation plate 300 to attach the vertebral fixation plate 300 to the vertebrae adjacent to the intervertebral space where the cage 200 is inserted.

Figure 13A:
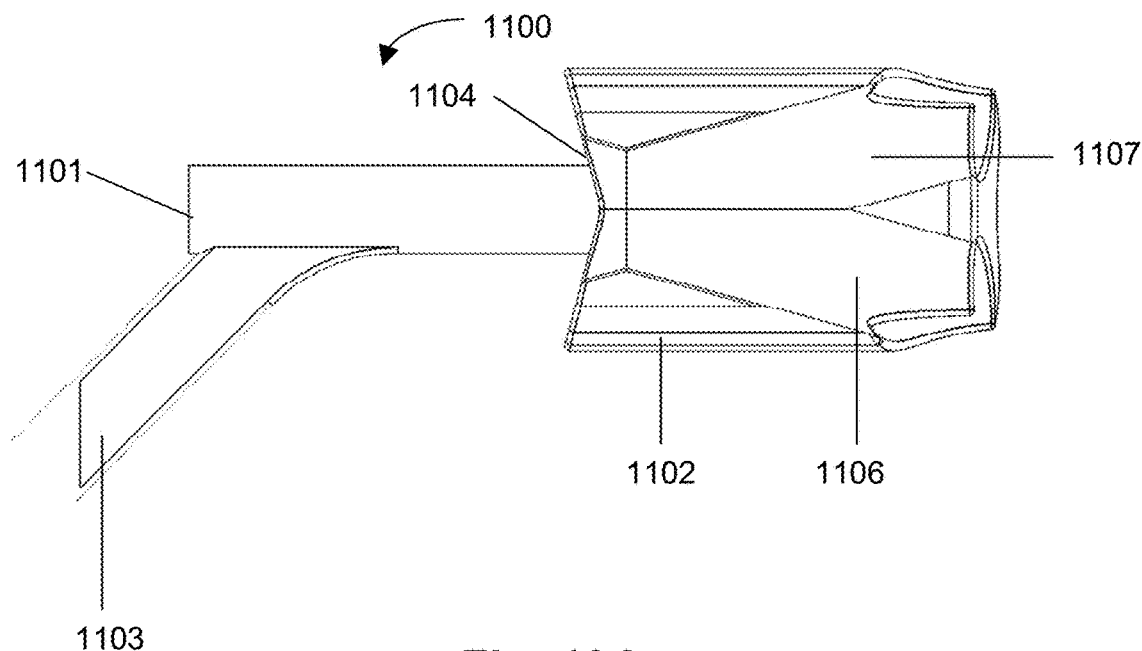
FIG. 13A is a cutaway view of a cage plate holder showing the drill guide channels within the drill guide assembly.
Figure 13B:
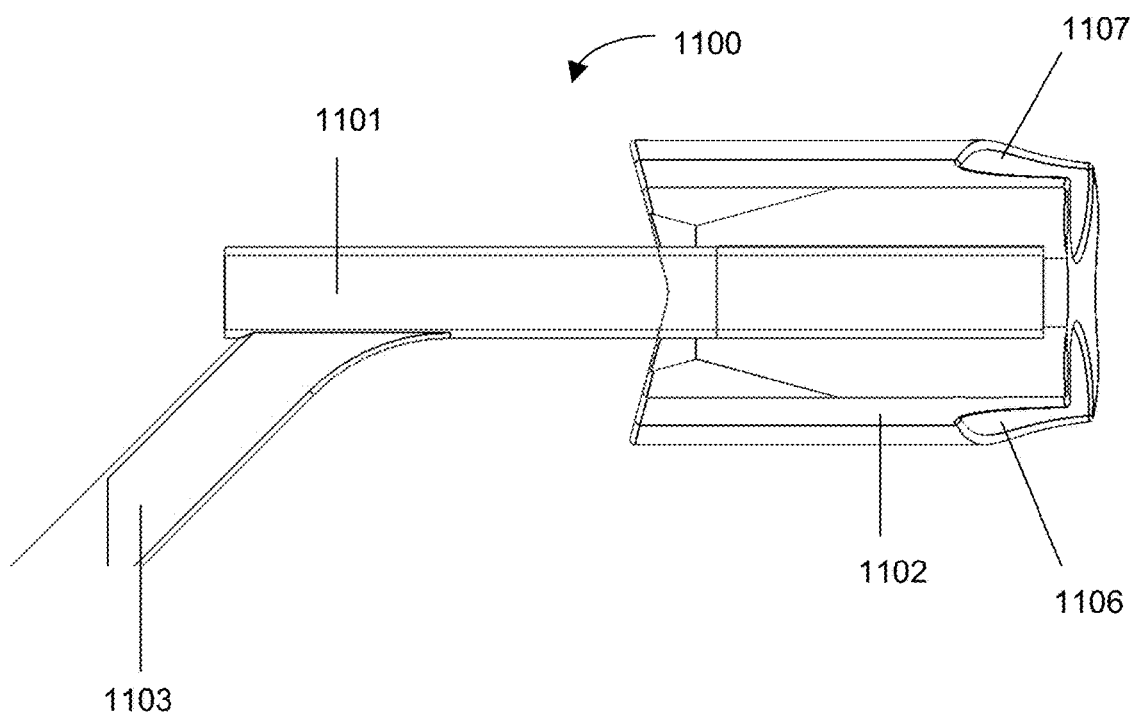
FIG. 13B is a cutaway view of a cage plate holder showing the central channel passing through the length of the cage plate holder and drill guide assembly.

FIG. 13 is a cutaway drawing of cage plate holder 1100 through a plane bisecting one of the openings 1104. The openings 1104 in drill guide assembly 1102 are formed in the shape of two intersecting cylinders 1106, 1107. As would be understood by a person of ordinary skill, other drill guides can be made in accordance with embodiments wherein more than four, three, or fewer than two cylinders are placed in drill guide assembly 1102, resulting in one or more openings 1104. So long as the openings 1104 in the drill guide allow a drill bit to pass through the opening 1104 and be constrained to a cylinder 1106/1107 allowing for alignment of the cylinder 1106/1107 with a hole in a vertebral fixation plate 311, the drill guide assembly will operate in accordance with the invention.

Figure 14:
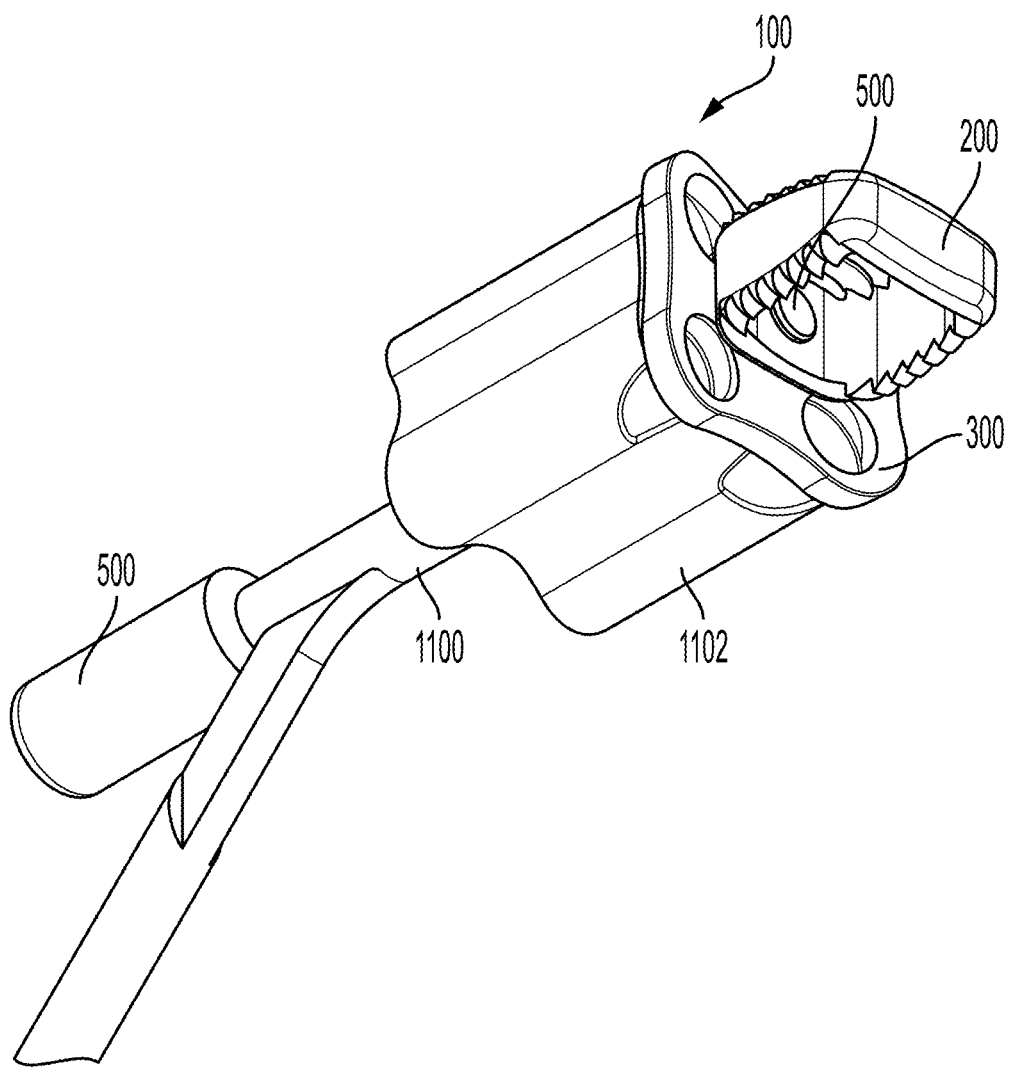
FIG. 14 is a view of an assembled modular intervertebral fixation device in accordance with an embodiment.
Figure 15:
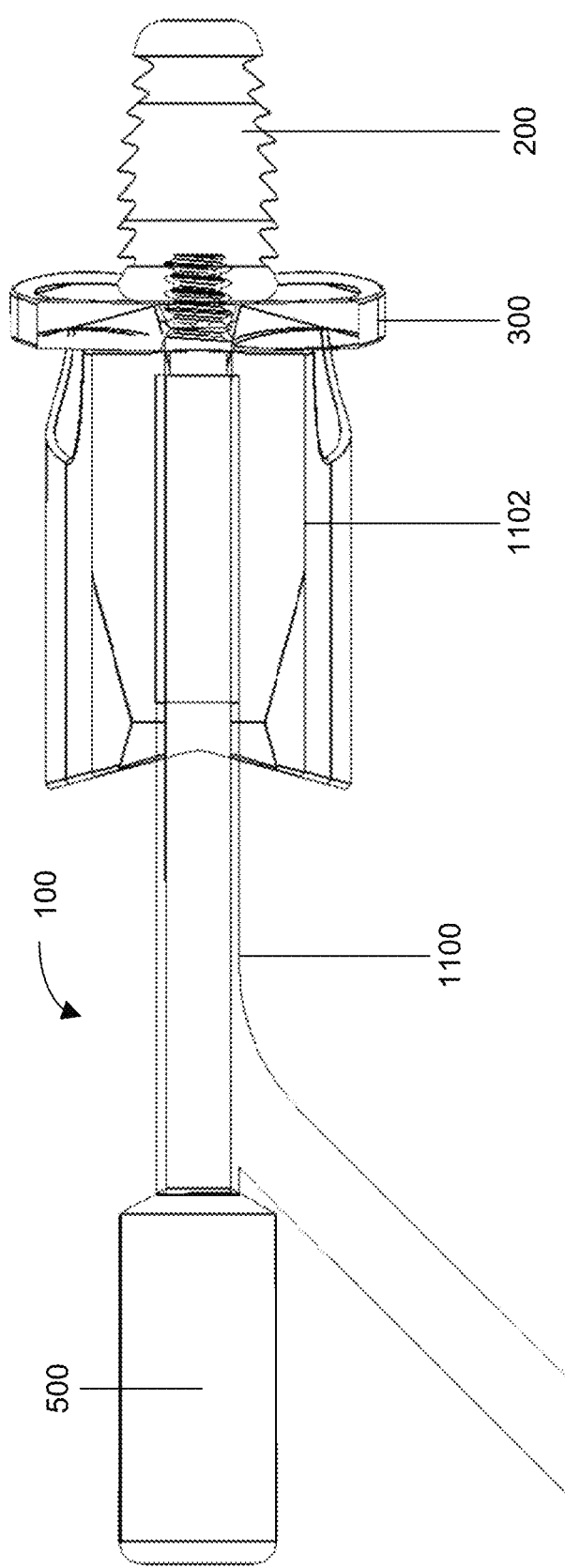
FIG. 15 is a cutaway view of an assembled modular intervertebral fixation device in accordance with an embodiment.

FIG. 14 is a cutaway drawing of a cage plate holder 1100 through a plane bisecting the central channel 1101. The central channel 1101 passes through the entire length of cage plate holder 1100, allowing a threaded pin 500 to be passed through the central channel 1101. Likewise, the distal openings of cylinders 1107 and 1106 in drill guide assembly 1102 are visible.

FIG. 14 depicts an assembled modular vertebral fixation device 100 in accordance with an embodiment. The fixation device 100 can be assembled by (1) inserting threaded handle 500 through the central channel 1101 of cage plate holder 1100, (2) placing a vertebral fixation plate 300 on the exposed end of threaded handle 500, and (3) attaching a cage by screwing the threaded end 501 of the threaded handle 500 into the orifice 206 of cage 200. The result is an assembled vertebral fixation device 100 that can be placed into an intervertebral space of a patient and affixed with minimal need for additional fixation pins or alignment devices.

FIG. 152 depicts a cutaway of assembled modular vertebral fixation device 100 through a plane bisecting threaded handle 500. This view shows threaded handle 500 passing through the cage plate holder 1100, through the vertebral fixation plate 300, and attaching to cage 200.

Figure 16A:
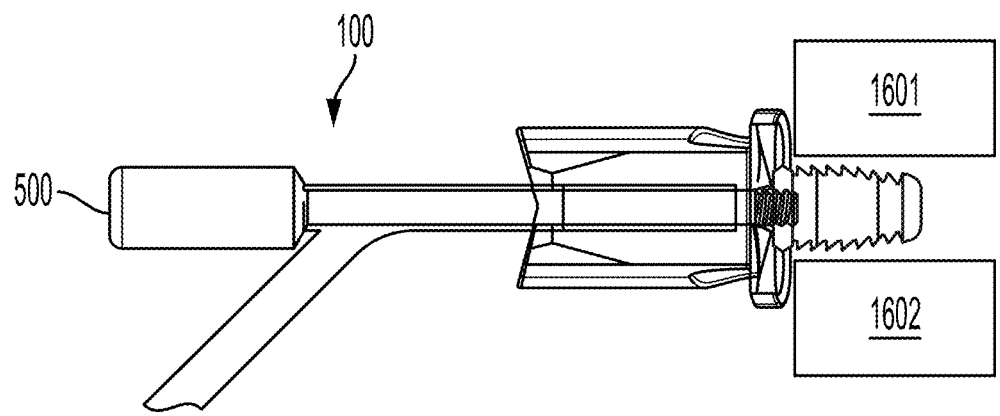
FIG. 16A depicts the insertion of the modular intervertebral fixation device into an intervertebral space.

FIGS. 16A-D illustrate the steps for installing an embodiment of the present invention in an intervertebral space of a patient. FIG. 16A shows an assembled vertebral fixation device inserted in an intervertebral space between vertebrae 1601 and 1602. Insertion can be facilitated by striking the impaction surface 504 of threaded handle 500. The cage 200 functions as a very secure temporary pin. The vertebral fixation plate 300 is not going to move or rotate as the holes are made and the screws placed. This can eliminate the need for temporary pins.

Figure 16B:
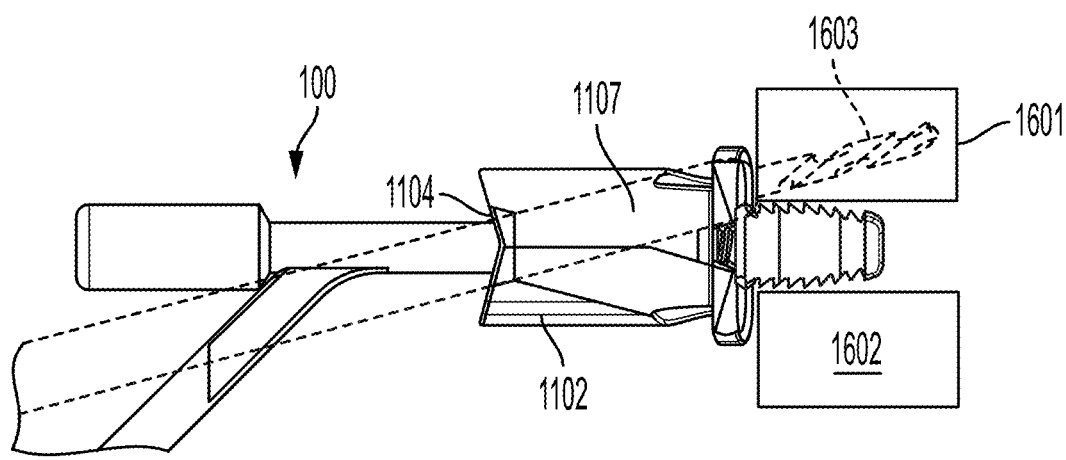
FIG. 16B depicts drilling holes in the vertebrae adjacent to the intervertebral space the modular intervertebral fixation device is inserted into using the drill guide assembly of the cage plate holder.

FIG. 16B depicts drilling a hole in vertebra 1601 by passing a drill bit 1603 into an opening 1104 and through cylinder 1107 of drill guide assembly 1102, and into vertebrae 1601. This process can be repeated a number of times for each bone screw 101 that will be inserted into fixation plate 300.

FIG. 16C depicts the installation of bone screws 101 into vertebral fixation plate 300. The bone screws 101 can be installed in fixation plate 300 by passing the screws through the opening 1104 in drill guide 1102. In some embodiments, this step can be performed with the modular vertebral fixation device 100 still fully-assembled.

FIG. 16D depicts the completed intervertebral fixation in a patient, with cage 200 disposed in the intervertebral space between vertebrae 1601 and 1602, and vertebral fixation plate 300 affixed to the vertebrae via bone screws 101. Following the insertion of the bone screws 101, the threaded handle 500 can be unscrewed from the cage 200, separating the cage plate holder 1100 and threaded handle 500 from the vertebral fixation plate 300 and cage 200. Once unscrewed, the threaded handle 500 and cage plate holder 1100 can be removed from the patient, leaving the vertebral fixation plate 300 affixed to the patients vertebrae 1601 and 1602, and holding the cage 200 in position.

Figure 17:
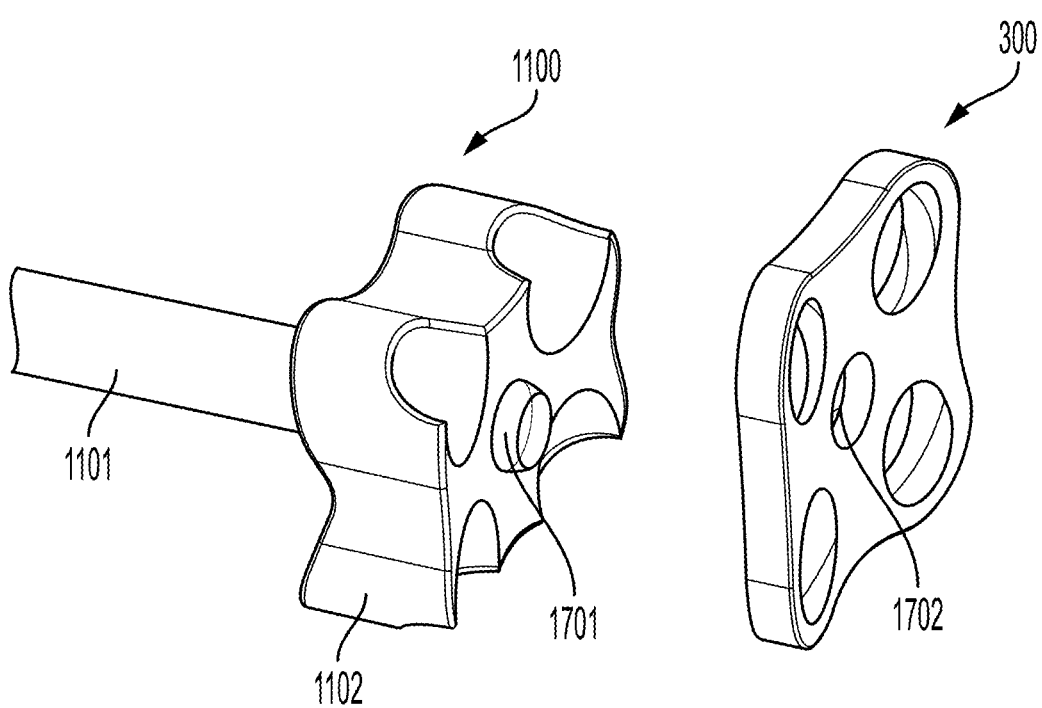
FIG. 17 depicts an embodiment of the cage plate holder and the intervertebral fixation plate with an interlocking feature.

FIG. 17 depicts an embodiment of the drill guide assembly 1102 of cage plate holder 1100, and a vertebral fixation plate 300. In this embodiment, the central channel 1101 passes through the drill guide assembly 1102, and has an interlocking feature 1701. Likewise, the vertebral fixation plate 300 has a corresponding interlocking feature 1702 which can interlock with the interlocking feature of drill guide assembly 1102. FIG. 17 depicts a specific embodiment where the interlocking feature is a rounded surface that mates with a corresponding rounded surface 1702 in vertebral fixation plate 300.

In some embodiments, the interlocking features of the cage plate holder and cage of the can be a rounded or chamfered surface, screw threads, or a snap-fit joint, or any other interlocking device as would be contemplated by a person having ordinary skill in the art. These interlocking features 1701 and 1702 can prevent misalignment of the vertebral fixation plate and the drill guides due to a loosening of the threaded rod 500 from the cage 200, or any unwanted play in the interface between the vertebral fixation plate 300 and the drill guide 1102. While the depicted interlocking rounded surface provides alignment in two axes of the drill guide with the vertebral fixation plate, other interlocking devices that can provide alignment in three axes are also contemplated. For example, interlocking feature 1701 or 1702 can have a key way that matches with a flat or other feature of the corresponding interlocking feature. Alternatively, one interlocking feature may be shaped like a gear, or any other shape, and the opposite interlocking feature can be a depression with a corresponding shape.

Figure 18:
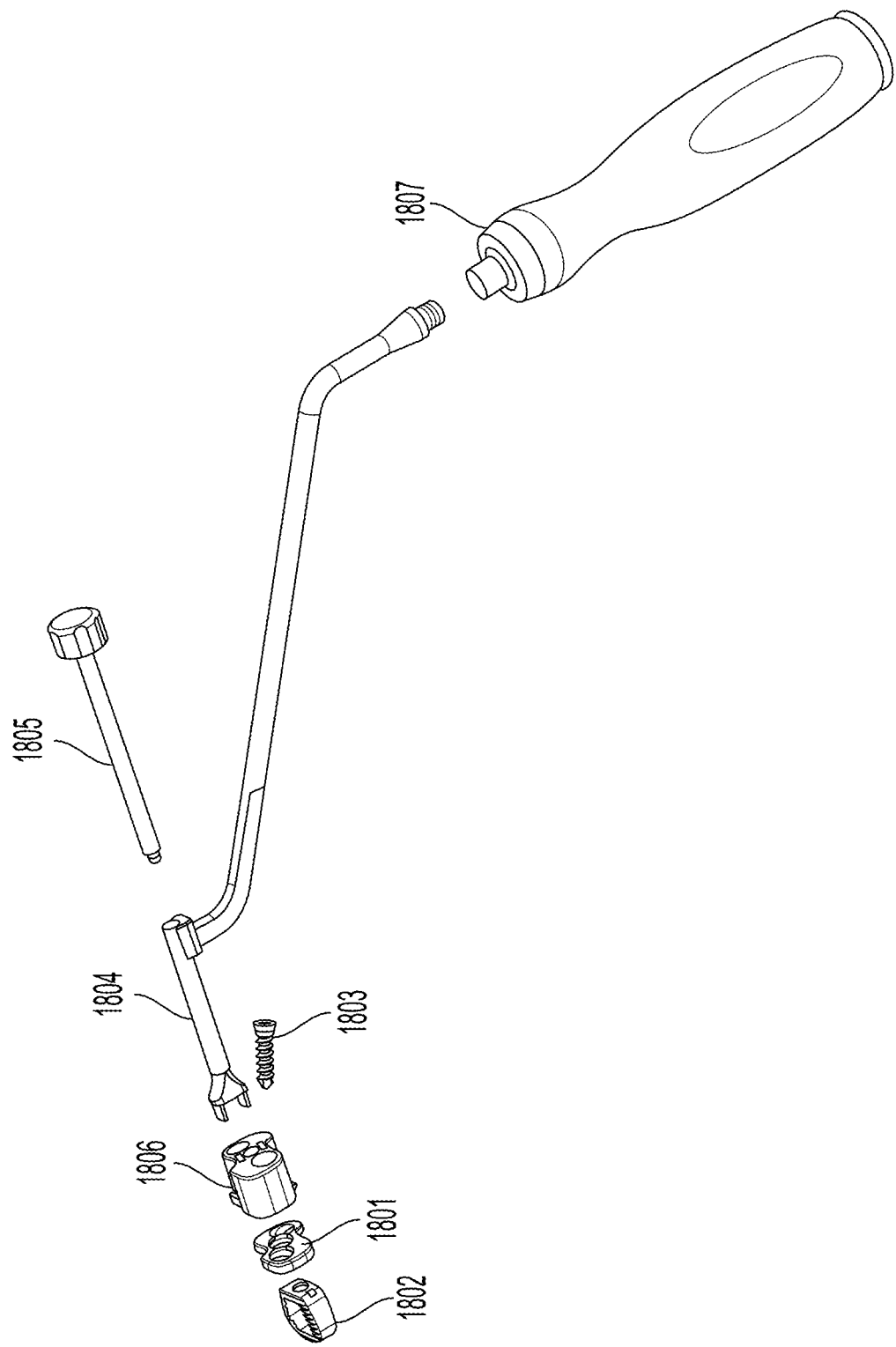
FIG. 18 depicts an embodiment of the intervertebral fixation system in accordance with an embodiment, including a detachable handle and detachable drill guide assembly.

FIG. 18 depicts the components of a vertebral fixation system in accordance with an embodiment. The fixation system can include a multi-screw vertebral fixation plate 1801, a cage 1802, and one or more bone screws 1803. The vertebral fixation system can be used to perform a spinal fusion procedure by inserting a cage 1802 filled with a bone growth factor or active biologic agent into the intervertebral space of a patient, and affixing the vertebra above and below the cage using a vertebral fixation plate 1801. To perform such a procedure, a surgeon can affix a cage 1802 and a vertebral fixation plate 1801 to a cage-plate holder 1804 using a threaded handle 1805. In some embodiments, the drill guide assembly 1806 can be detached from the cage-plate holder 1804. This functionality enables the same cage-plate holder 1804 to be used with a variety of drill guide assemblies 1806 that may be designed to provide appropriate drilling locations for a cage 1802, vertebral fixation plate 1801, or for a particular patient's anatomical structure or surgical location, among other reasons.

Additionally, the cage plate holder 1804 may further comprise a detachable handle 1807. By providing a detachable handle 1807, a variety of handles 1807 can be used with cage plate holder 1804. Alternatively, the detachable aspect of detachable handle 1807 can allow the cage plate holder 1804 and handle 1807 to be stored in a smaller space.

Figure 19:
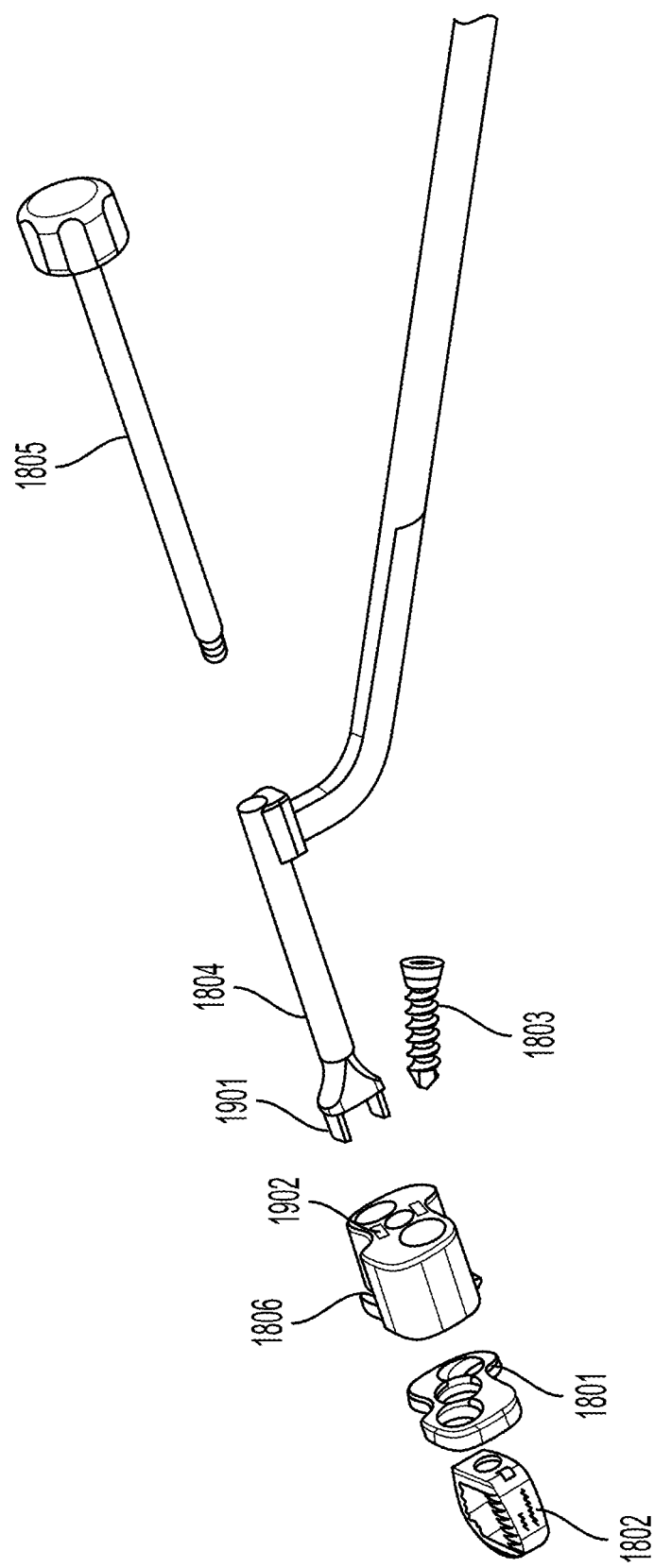
FIG. 19 depicts further details of the embodiment shown in FIG. 18.

FIG. 19 is a detailed view of the embodiment of FIG. 18. The cage plate holder 1804 can further comprise a peg 1901 which can be inserted into a corresponding slot 1902 of the drill guide assembly 1806. As shown, there are two pegs 1901 and two slots 1902; however, as would be understood by a person of ordinary skill in the art, a single peg 1901 and a single slot 1902 can be used. Alternatively cage plate holder 1804 and drill guide assembly 1806 can be connected in a variety of ways, including providing corresponding internal and external screw threads on the distal end of the cage plate holder 1804 and the proximal end of the drill guide assembly 1806. Alternatively, a corresponding keyway and key can be used to interlock cage plate holder 1804 and drill guide assembly 1806. Further, any mechanism that attaches the cage plate holder 1804 to the drill guide assembly 1806 can be used, so long as the mechanism fixes the spatial relationship between the cage plate holder 1804 and the drill guide assembly 1806.

Figure 20:
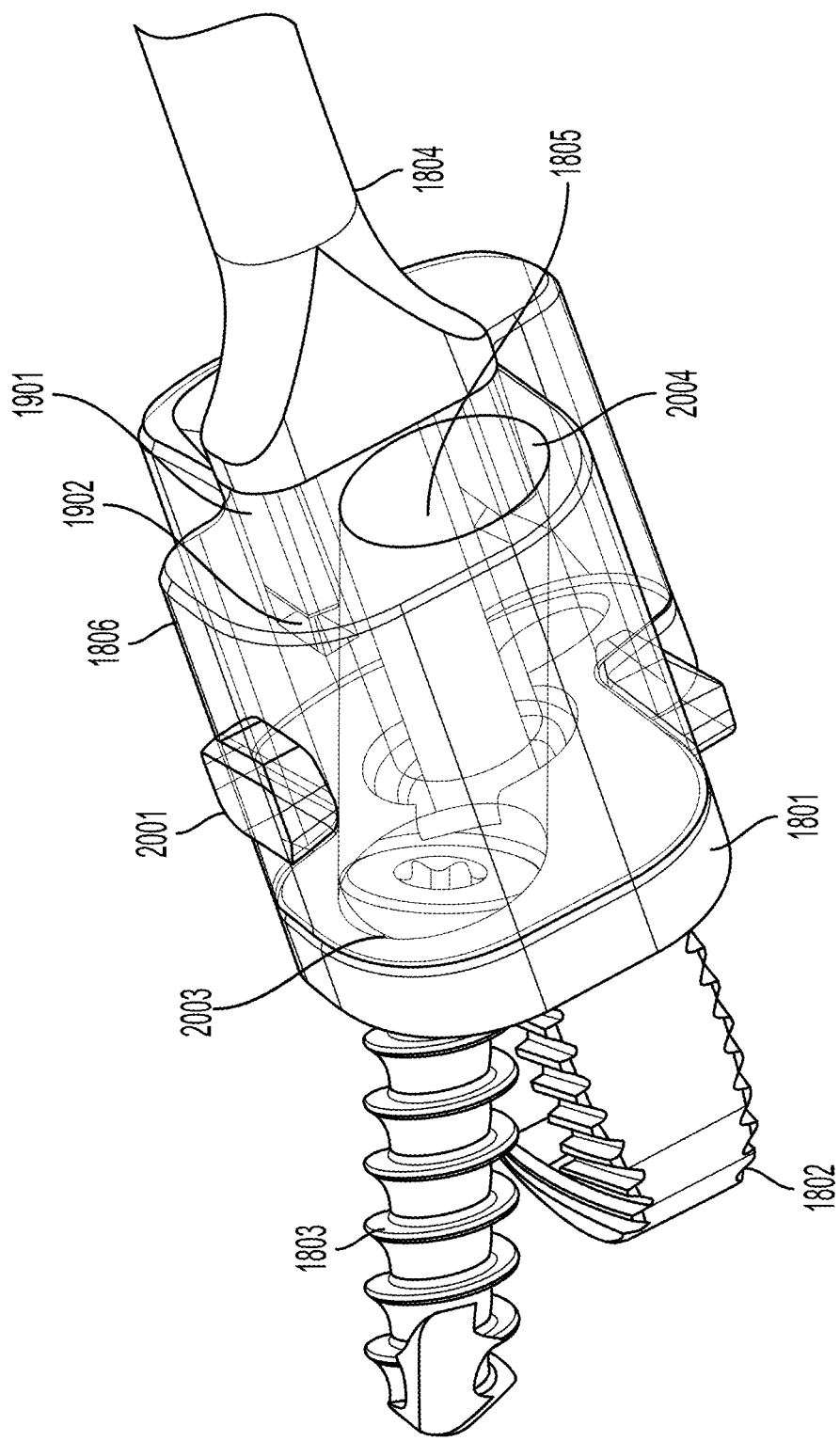
FIG. 20 depicts an assembled intervertebral fixation system in accordance with the embodiment depicted in FIG. 18.

FIG. 20 depicts the details of an assembled cage plate holder 1804, drill guide assembly 1806, vertebral fixation plate 1801, and cage 1802. The cage plate holder 1804 is affixed to the cage 1802 by the threaded handle 1805. The drill guide assembly 1806 is affixed to the cage plate holder 1804 by the insertion of tab 1901 into slot 1902. In some embodiments, the drill guide can comprise one or more flanges 2001 which limit the rotational motion of the vertebral fixation plate 1801. As would be recognized by a person of ordinary skill in the art, any feature, including flanges, can be used to prevent the vertebral fixation plate 1801 from rotating with respect to the drill guide assembly 1806. These features further can ensure that the openings 2004 of the drill guide assembly 1806 remain in alignment with the openings 2003 of the vertebral fixation plate to allow screws 1803 and other tools to pass through the opening of the drill guide assembly 1806 and vertebral fixation plate 1801.

Figure 22:
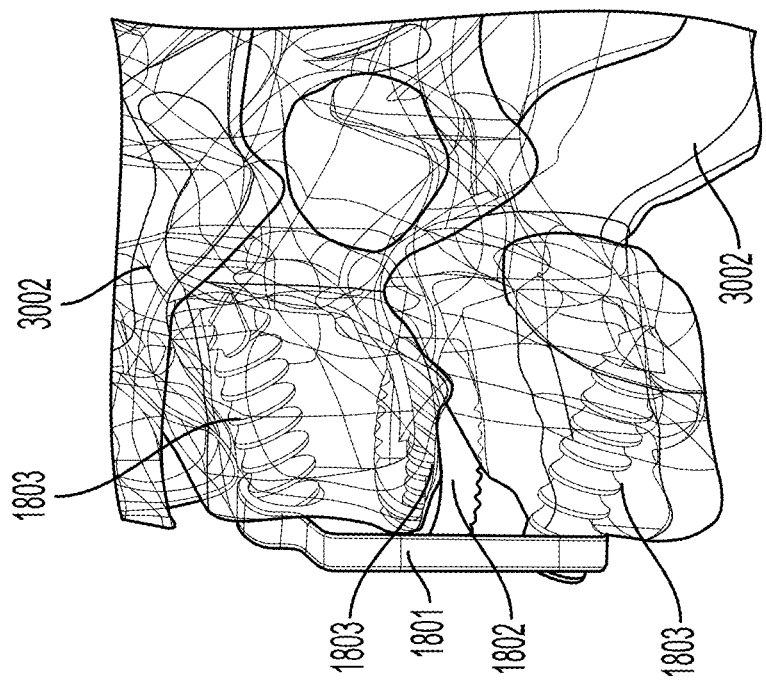
FIG. 22 depicts a side-view of the installed cage, vertebral fixation plate, and screws of FIG. 21.
Figure 21:
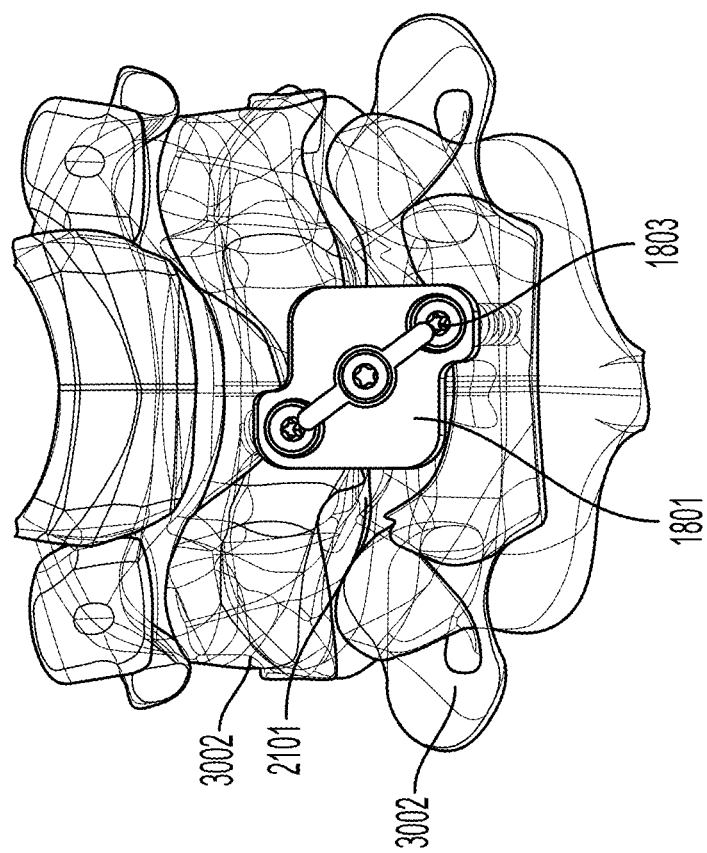
FIG. 21 depicts a rear view of an installed cage, vertebral fixation plate, and screws.

FIGS. 21 and 22 depict a vertebral fixation plate 1801 and cage 1802 installed into the spine of a patient using a device according to an embodiment. Here, the vertebral cage 1802 is installed into an intervertebral space of a patient 2101, with screws 1803 inserted into adjacent vertebrae 3002.

Figure 23:
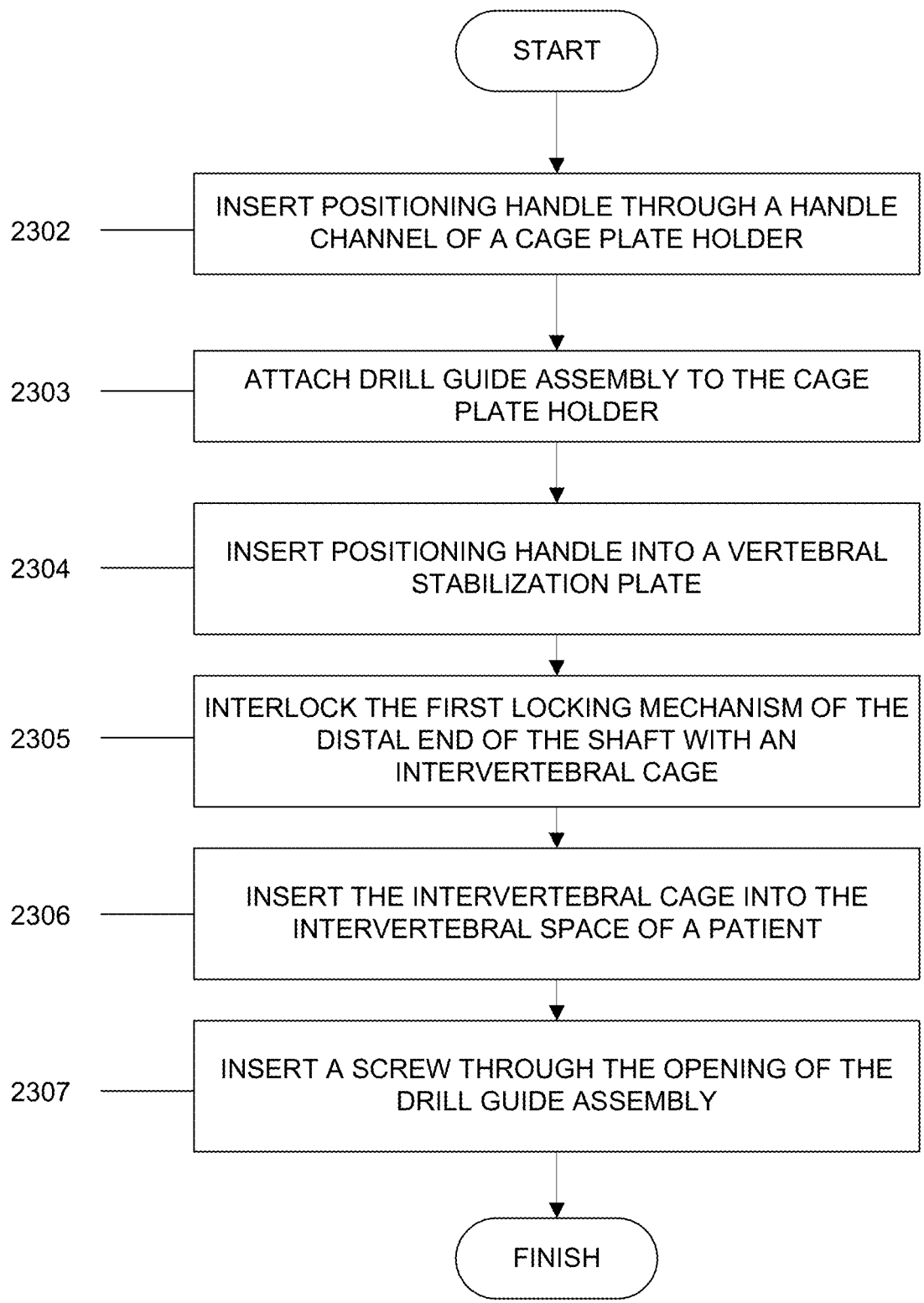
FIG. 23 depicts a method for using a vertebral fixation system in accordance with an embodiment.

FIG. 23 depicts a method for using a vertebral stabilization system in accordance with an embodiment. The method begins by inserting a positioning handle 104 through a handle channel 1101 of the cage-plate holder 1100, 2302. Then, a surgeon can optionally attach a drill guide assembly to the cage-plate holder 2303. For embodiments where the drill guide assembly is permanently affixed to the cage-plate holder, this step 2303 can be omitted. Then the surgeon can insert the positioning handle 104 into a vertebral stabilization plate 2304. This step may further comprise the attachment of flanges or other interlocking devices of the drill guide assembly 1806 and the cage 1802, as described above. Next, the distal end of the shaft of the positioning handle 501 can be interlocked with the second locking mechanism of the intervertebral cage 1082, 2305. Next, the intervertebral cage can be inserted into the intervertebral space of a patient 2306. Finally, a screw 1803 can be inserted through the opening of the drill guide assembly and into a vertebra of a patient 2307. Following these steps, the interlocking mechanisms of the distal end of the shaft of the positioning handle and the proximal end of the vertebral cage can be disconnected, freeing the vertebral cage plate from the cage-plate holder 1100 and drill guide assembly 1102.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A vertebral stabilization system comprising:
    a positioning handle comprising a shaft with a distal end and a proximal end, the distal end of the shaft comprising a first locking mechanism;
    a holder comprising a handle channel and a drill guide, the drill guide comprising a drill opening extending from a proximal end to a distal end of the drill guide, wherein the drill opening is configured to accept a drill; and
    an implant comprising a distal end, a proximal end, and an opening, wherein the proximal end comprises an orifice with a second locking mechanism configured to engage with the first locking mechanism, wherein at least a portion of the shaft can be inserted through the handle channel and into the orifice, and wherein engagement of the first locking mechanism and the second locking mechanism secures the implant to the holder.

2. The vertebral stabilization system of claim 1, further comprising a fastener plug comprising a third locking mechanism configured to engage with the second locking mechanism.

3. The vertebral stabilization system of claim 2, wherein: the first locking mechanism and the third locking mechanism comprise external screw threads; and the second locking mechanism comprises internal screw threads sized to engage with the external screw threads.

4. The vertebral stabilization system of claim 2, wherein the fastener plug is shearable and comprises a shearable zone which breaks when a shearing force is applied to a head of the fastener plug.

5. The vertebral stabilization system of claim 2 further comprising a vertebral stabilization plate comprising a handle hole, wherein the fastener plug is simultaneously engageable with the handle hole and the orifice to create a fluid-tight seal at a junction between the fastener plug, the handle hole, and the orifice.

6. The vertebral stabilization system of claim 5, wherein the fastener plug comprises a cannulation and a re-sealing opening, wherein the cannulation is sized to accept a tip of a syringe.

7. The vertebral stabilization system of claim 2, wherein the fastener plug comprises a cannulation sized to accept a tip of a syringe.

8. The vertebral stabilization system of claim 1, wherein the drill guide is modular and is detachably attachable to the holder.

9. The vertebral stabilization system of claim 1, wherein the first locking mechanism comprises a keyway, wherein the second locking mechanism comprises a first keyhole, wherein the second locking mechanism comprises a second keyhole, and wherein the keyway is configured to engage with the first keyhole and the second keyhole.

10. The vertebral stabilization system of claim 1, wherein the drill guide is integrated with the holder.

11. A method for stabilizing a vertebral column comprising:
    inserting a positioning handle into an implant, the positioning handle comprising a shaft with a distal end and a proximal end, the distal end of the shaft comprising a first locking mechanism;
    engaging the first locking mechanism with a second locking mechanism of the implant, the implant comprising a distal end, a proximal end, and an opening, wherein the proximal end of the implant comprises an orifice with the second locking mechanism, and wherein the opening of the implant extends from a superior side of the implant to an inferior side of the implant;
    inserting the implant into an intervertebral space of a patient;
    inserting the positioning handle through a handle channel of a holder comprising a drill guide; and
    inserting a screw through at least a portion of the implant; wherein inserting the screw comprises inserting the screw through a drill opening in the drill guide.

12. The method of claim 11, further comprising inserting a fastener plug into the orifice.

13. The method of claim 12, wherein the fastener plug comprising a third locking mechanism configured to engage with the second locking mechanism, and wherein inserting the fastener plug into the orifice comprises engaging the third locking mechanism with the second locking mechanism.

14. The method of claim 12, further comprising applying a force to shear a shearable portion of the fastener plug after inserting the fastener plug into the orifice.

15. The method of claim 12, further comprising:
    inserting a tip of a syringe into a cannulation of the fastener plug; and
    delivering a fluid through the cannulation.

16. The method of claim 15, further comprising applying a force to shear a shearable portion of the fastener plug after delivering the fluid.

17. The method of claim 15, wherein inserting the tip of the syringe into the cannulation of the fastener plug comprises inserting the tip through a re-sealing opening within the cannulation.

18. The method of claim 11, further comprising:
inserting a tip of a syringe into a syringe receptacle in the proximal end of the positioning handle; and
delivering a fluid through a fluid channel traversing a length of the positioning handle, through the orifice of the implant, and into the opening of the implant without removing the positioning handle from the implant.

19. A method for stabilizing a vertebral column comprising:
inserting a positioning handle through a holder and into an implant, the positioning handle comprising a shaft with a distal end and a proximal end, the holder comprising a first interlocking mechanism engageable with a second interlocking mechanism of the implant, and the implant comprising a distal end, a proximal end, and an opening, wherein the proximal end of the implant comprises an orifice with the second interlocking mechanism, and wherein the opening of the implant extends from a superior side of the implant to an inferior side of the implant;
engaging the first interlocking mechanism with the second interlocking mechanism;
inserting the implant into an intervertebral space of a patient;
inserting a tip of a syringe into a syringe receptacle in the proximal end of the positioning handle; and
delivering a fluid through a fluid channel traversing a length of the positioning handle, through the orifice of the implant, and into the opening of the implant without removing the positioning handle from the implant or the holder.

* * * * *